(12) United States Patent
Thiel et al.

(10) Patent No.: US 10,828,068 B2
(45) Date of Patent: Nov. 10, 2020

(54) BONE PLATE, SURGICAL SETS AND RECONSTRUCTION SETS

(71) Applicant: MEDARTIS HOLDING AG, Basel (CH)

(72) Inventors: Dirk Thiel, Staufen (DE); Andreas Mullis, Tenniken (CH); Jürgen Schonhardt, Rheinfelden (DE); Hermann Zeuner, Freiburg (DE); Simon Martin Schätzle, Gottenheim (DE)

(73) Assignee: MEDARTIS HOLDING AG, Basel (CH)

( * ) Notice: Subject to any disclaimer, the term of this patent is extended or adjusted under 35 U.S.C. 154(b) by 524 days.

(21) Appl. No.: 15/536,430

(22) PCT Filed: Dec. 17, 2014

(86) PCT No.: PCT/EP2014/078136
§ 371 (c)(1),
(2) Date: Jun. 15, 2017

(87) PCT Pub. No.: WO2016/095978
PCT Pub. Date: Jun. 23, 2016

(65) Prior Publication Data
US 2017/0348023 A1    Dec. 7, 2017

(51) Int. Cl.
*A61B 17/80*     (2006.01)
*A61B 17/68*     (2006.01)
(Continued)

(52) U.S. Cl.
CPC ........ *A61B 17/683* (2013.01); *A61B 17/8052* (2013.01); *A61B 17/8071* (2013.01);
(Continued)

(58) Field of Classification Search
CPC combination set(s) only.
See application file for complete search history.

(56) References Cited

U.S. PATENT DOCUMENTS 4,726,808 A    2/1988 Collins
4,903,691 A    2/1990 Heinl
(Continued)

FOREIGN PATENT DOCUMENTS

CH    S69 105 A5    2/1989
CH    675 531 A5    10/1990
(Continued)

OTHER PUBLICATIONS

US 9,125,700 B2, 09/2015, Olms et al. (withdrawn)
(Continued)

*Primary Examiner* — Sameh R Boles
(74) *Attorney, Agent, or Firm* — Davis & Bujold PLLC; Michael J. Bujold

(57) ABSTRACT

A bone plate for reconstruction or trauma treatment of a bone which comprises first and second ends, a first contact surface for contacting and securing on a first region of the bone, and a plurality of receiving mechanism each having at least one opening for receiving at least one securing element. At least two adjacent wings extend at least from the first end of the main section, each has a second contact surface for contacting and securing to a second region of the bone, as well as at least one receiving mechanism having at least one opening for each receiving a securing element. A minimum bending stiffness of the main section, in relation to an axis (x) running perpendicular to the first contact surface, is greater than the minimum bending stiffnesses of the wings, but smaller than the total minimum bending stiffness of all wings extending from the first end.

16 Claims, 20 Drawing Sheets

(51) Int. Cl.
*A61F 2/28* (2006.01)
*A61B 17/86* (2006.01)

(52) U.S. Cl.
CPC ...... *A61B 17/8085* (2013.01); *A61B 17/8635* (2013.01); *A61B 17/8645* (2013.01); *A61F 2/2803* (2013.01); *A61B 17/8057* (2013.01); *A61B 2017/8655* (2013.01); *A61F 2002/2807* (2013.01)

(56) References Cited

U.S. PATENT DOCUMENTS

| | | |
|---|---|---|
| 5,674,222 A | 10/1997 | Berger et al. |
| 6,129,728 A | 10/2000 | Schumacher et al. |
| 6,506,191 B1 | 1/2003 | Joos |
| 6,730,091 B1 | 5/2004 | Pfefferle et al. |
| 6,960,211 B1 | 11/2005 | Pfefferle et al. |
| 8,292,898 B2 | 10/2012 | Castaneda et al. |
| 8,672,981 B2 | 3/2014 | Jacobs |
| 8,911,482 B2 | 12/2014 | Lee et al. |
| 9,066,733 B2 | 6/2015 | Furrer et al. |
| 9,066,767 B2 | 6/2015 | Buchbinder et al. |
| 9,155,577 B2 | 10/2015 | Pfefferle et al. |
| 2005/0090825 A1 | 4/2005 | Pfefferle et al. |
| 2005/0124472 A1 | 6/2005 | Carlucci et al. |
| 2005/0234472 A1 | 10/2005 | Huebner |
| 2007/0043366 A1* | 2/2007 | Pfefferle ............ A61B 17/8052 606/279 |
| 2007/0238069 A1 | 10/2007 | Lovald et al. |
| 2009/0138051 A1 | 5/2009 | Olms et al. |
| 2009/0281543 A1 | 11/2009 | Orbay et al. |
| 2009/0299369 A1 | 12/2009 | Orbay et al. |
| 2009/0312802 A1 | 12/2009 | DaSilva |
| 2011/0144698 A1 | 6/2011 | Buchbinder et al. |
| 2011/0160730 A1* | 6/2011 | Schonhardt ........ A61B 17/8061 606/71 |
| 2013/0096559 A1 | 4/2013 | Katrana et al. |

FOREIGN PATENT DOCUMENTS

| | | |
|---|---|---|
| DE | 36 01 715 A1 | 7/1987 |
| DE | 103 35 281 A1 | 7/2004 |
| DE | 10 2010 048 052 A1 | 4/2012 |
| DE | 10 2014 107 495 A1 | 12/2015 |
| EP | 1 182 972 B1 | 10/2003 |
| EP | 1 107 699 B1 | 11/2003 |
| EP | 1 468 656 A1 | 10/2004 |
| EP | 2 792 324 A1 | 10/2014 |
| FR | 2622431 A1 | 5/1989 |
| JP | 2003509093 A | 3/2003 |
| JP | 2003530138 A | 10/2003 |
| JP | 2009500093 A | 1/2009 |
| JP | 2012502687 A | 2/2012 |
| JP | 2013513438 A | 4/2013 |
| JP | 2013524995 A | 6/2013 |
| RU | 2 033 105 C1 | 4/1995 |
| WO | 00/66012 A1 | 11/2000 |
| WO | 01/82809 A1 | 11/2001 |
| WO | 03/068091 A1 | 8/2003 |
| WO | 2004/086990 A1 | 10/2004 |
| WO | 2010/080511 A1 | 7/2010 |
| WO | 2013/096592 A1 | 6/2013 |

OTHER PUBLICATIONS

Japanese Office Action issued in corresponding Japanese Patent Application No. 2017-532957 dated Oct. 2, 2018.
International Search Report Corresponding to PCT/EP2014/078136 dated Oct. 7, 2015.
Written Opinion Corresponding to PCT/EP2014/078136 dated Oct. 7, 2015.
European Search Report Corresponding to 19203806.5 dated Feb. 5, 2020.

* cited by examiner

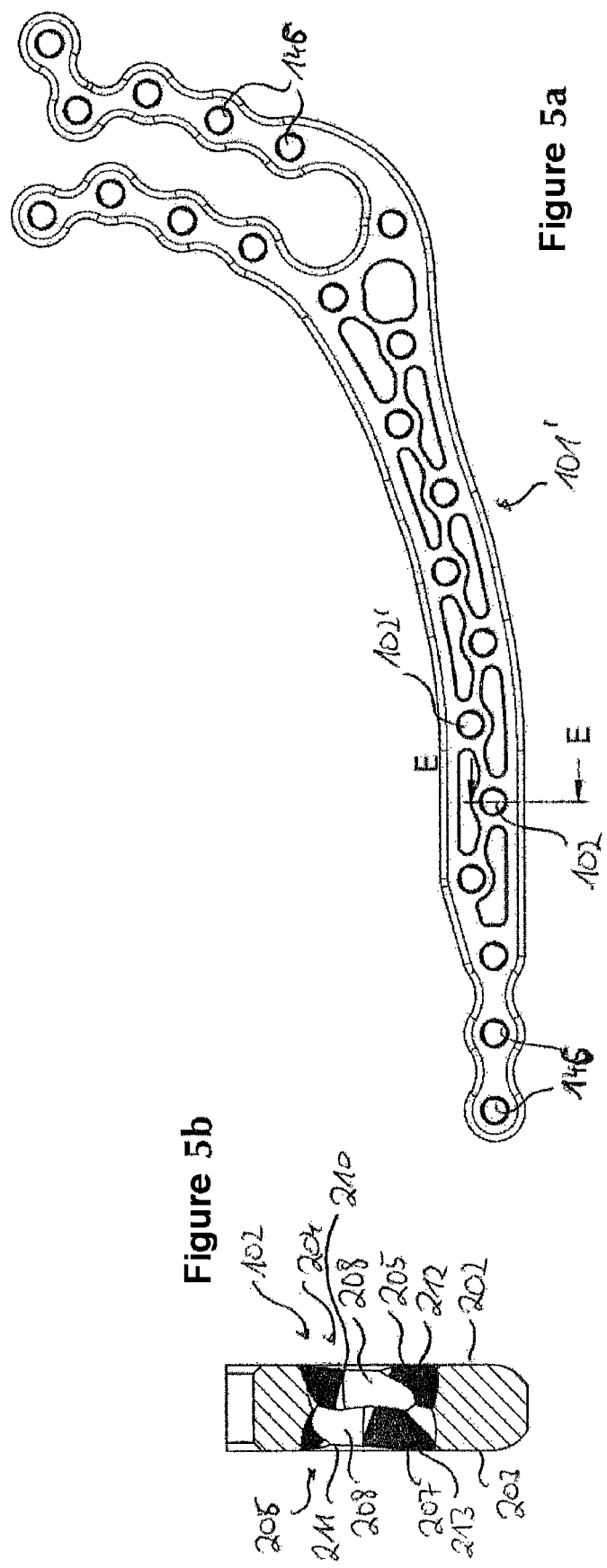

BONE PLATE, SURGICAL SETS AND RECONSTRUCTION SETS

The present invention concerns bone plates, surgical sets and reconstruction sets according to the preambles of the independent claims. Such bone plates can be used to bridge a bone defect or rather to treat a fracture. In particular, the invention concerns bone plates for the reconstruction of or the trauma treatment of a human mandible.

In the case of treating unstable comminuted fractures, with reconstructions with bone transplants and, in particular, in the case of bridging bone defects without any bone transplant, stable bone plates are required by means of which the loads occurring in the defect region are reliably absorbed. A generic bone plate for a human mandible is disclosed, for example, in WO 01/82809. For example, weakened, healed bone structures of a mandible can be strengthened using such plates. Such bone structures can be caused, for instance, when a tumor is removed or also by an injury, for example by a gun shot. The bone plate is to be able to withstand the daily loads which occur, for example, when chewing or swallowing, over a long period. In order for the bone plate not to bend in a noticeable manner in this connection, it has to exhibit a certain rigidity. A hard material is usually used for this purpose, such as, for example, grade 4 titanium. Said grade titanium is, on the one hand, very hard and consequently rigid in relation to bending, on the other hand, however, it is also relatively brittle.

The anatomy of human bones and, in particular, of a human mandible, however, is individually very different. The distance between the mandible angle, which is formed between ascending ramus and horizontal ramus, and the center point of the chin, thus varies somewhat, for example in dependence on age, size and sex of the patient. As a result of the individually occurring variations in the bone form, in particular on the human mandible, anatomically moldable plates or specially prepared patient-specific plates are required. From a practical viewpoint, it is consequently hardly possible for a hospital or a surgeon to keep a pre-molded, suitable bone plate in storage for every anatomy. Instead, the surgeon has to adapt the bone plate to the individual anatomy of the patient by cutting and bending.

Various therapy approaches have been followed up to now. The three most important treatment methods treat the described defects with moldable mini-plates, with specially moldable reconstruction plates and, as already mentioned, with specially prepared patient-specific plates.

Mini-plates, such as, for example, those disclosed in WO 00/66012 A1 and WO 03/068091, are bone plates with a relatively small material thickness. The advantage of these is that they are already widely used as standard plates for simple and easily repairable fractures and can be used in a flexible manner especially on the mandible. The mini-plates can be easily molded onto the bone fragments using simple bending instruments. However, mini-plates comprise certain limits on account of their material thickness particularly in the case of a heavier load. Use in the case of the above-mentioned indications often results post-operatively in plate breakages and dislocations.

This is where the advantages of reconstruction plates come in: reconstruction plates are relatively solid plates, typically produced from a hard grade titanium or from titanium alloys with a material thickness of between 2.0 to 3.5 mm, which are very sturdy and are able to absorb high forces. Said reconstruction plates are usually realized such that the bending regions are located between the fastening openings, the openings and bending regions being put together in the manner of a pearl necklace. The plate is able to be adapted anatomically to the bone fragments, from opening to opening, as a result of the bending regions.

However, reconstruction plates, in spite of their specially realized deforming regions, can only be adapted with difficulty to the respective bone form, in particular in the region of the ascending ramus of a mandible. Very high forces are required to bend the plates on account of the material thickness and the material strength. The bending tools have to be realized in a very solid, precisely-fitting manner and have corresponding movement paths on account of the large necessary forces.

The molding of the plates is additionally very time-consuming and requires a good deal of experience on the part of the operator. For, in particular, the bone plates cannot be molded directly on the mandible of the patient. As the bone plate has to have a certain rigidity for the above-mentioned reasons, very high forces, which could make the already-existing bone defect even worse, should be applied. The surgeon has first of all to measure the individual anatomy of the mandible in a rough manner and then bend the bone plate appropriately externally of the patient more or less as judged visually, which usually occurs using one or several bending pliers. As an alternative to this, so-called templates, that is to say soft metal plates, can also be used. These are bent onto the mandible as a template and the bone plate to be bent is bent, in turn, in the described manner by way of said template externally of the patient.

However, such bending using bending pliers is generally not very precise. This is in particular as the bone plate is generally not to extend in one plane. It may therefore happen that the appropriately bent bone plate has not been adapted or has only been adapted insufficiently to the mandible. In this case, the surgeon has to perform several adapting steps. On account of the inherent brittleness of the material (for example grade 4 titanium), this is only possible a few times. There could, namely, be the risk of the material of the bone plate being weakened as a result of the multiple bending in such a manner that it can break either during the operation or post-operatively in the patient.

In addition, strain hardenings and micro-fissures can occur on account of the molding. Especially in the case of plates for the mandible, the highly varying angle between the corpus and the ascending ramus makes a high degree of deformation of the plates necessary within the mandible angle region. This increases the above-mentioned formation of micro-fissures and often results post-operatively in plate breakages increasingly in the region of the strong deformations.

To this, it must be added that as a result of arranging the openings side by side, the bone screw close to the fracture or the defect has to absorb the greatest load. On account of said point-type high load, the result post-operatively is often screw breakages or osteonecrosis in the region of the bone screw close to the fracture or the defect. Especially in the case of bridging osseous defects, soft tissue irritation or even soft tissue necroses occur in the region of the bridge as a result of the saw-tooth-like outside contours of the reconstruction plates.

In addition, when bending a bone plate, which is disclosed, for example, as in WO 01/82809, using bending pliers, unwanted bending inside the plate plane or unwanted torsion can occur.

Patient-specifically prepared implants can eliminate the above-mentioned disadvantages of the mini-plates and reconstruction plates, but they are very expensive in planning and preparation such that a certain number of experts is necessary for their production. To this, it must be added that patient-specifically prepared implants can only be used sensibly for plannable interventions and are relatively expensive compared to series-produced plates.

U.S. Pat. No. 4,726,808 discloses mandible plates with a center portion and two wings which extend therefrom and can be arranged on oppositely situated sides of a ramus. The prosthesis is realized in a substantially strip-shaped manner in a center portion and includes openings for bone screws, which openings are arranged along a center line of the center portion. However, the arrangement of the wings on oppositely situated sides of a ramus is complex. In addition, said plates can only be molded to the individual anatomy of a patient with difficulty, in particular in the region of the ascending ramus. In order, therefore, to be able to provide a suitable bone plate for possibly any defect without having to accept the above-mentioned risks (such as, for example, the risk of micro-fissures if there is too much deformation), a large range of different bone plates must always be held in store, which is expensive and cost-intensive.

Document RU 2 033 105 C1 discloses a bone plate for treating mandible fractures in the region of the symphysis. The bone plate shown in the figures comprises a type of truss structure. However, fixing into the region of the ramus using said bone plate is not possible. In addition, said bone plate also can only be molded onto the individual anatomy of a patient with difficulty such that a large range of different bone plates must always be held ready.

WO 2010/080511 A1 discloses three-dimensional truss implants (but no generic bone plates) which can replace, for example, part of a mandible. Simple adaptability to the individual anatomy of a patient, however, is not provided here either such that a large range of different bone plates must always be held ready. In addition, said truss implants are not designed to withstand the bending forces, which occur, for example, when chewing and swallowing, arising within the plate plane above all in the region of the ascending ramus.

WO 2013/096592 A1 also discloses devices and methods for promoting bone growth which comprise a trabeculae-like grid structure which is to promote bone growth. Generic bone plates are therefore not disclosed. In addition, there is no simple adaptability to the individual anatomy of a patient here either. In addition, said structures are not designed to withstand the bending forces, which occur, for example, when chewing and swallowing, arising within the plate plane above all in the region of the ascending ramus.

Document DE 103 35 281 A1 discloses a grid arrangement for osteosyntheses. The bone plates shown in FIGS. 1 to 3 include double rows of screw holes which are arranged in each case in a straight line and are connected via webs which extend diagonally between them to form a flat grid arrangement. Said grid arrangement, however, can also only be molded to the individual anatomy of a patient with difficulty. In addition, said grids are not designed to withstand the bending forces, which occur, for example, when chewing and swallowing, arising within the plate plane above all in the region of the ascending ramus. In addition, for instance, the outside edges of the ring-shaped receiving means for the bone screws comprise edges which are unpleasant for the patient and could even result in an injury to the body tissue.

EP 1 182 972 B1 discloses osteosynthetic bone plates for treating fractures, in particular mandible fractures. Said bone plates can also only be adapted to the individual anatomy of a patient with difficulty without a large range of different bone plates having to be held ready for this purpose.

In light of the disadvantages described beforehand, it is an object of the present invention to provide a bone plate which does not comprise said disadvantages. In particular, the bone plate is to be easily moldable to the individual anatomy of a patient without an excessively large range of different bone plates having to be held ready or the risk of the formation of micro-fissures or strain hardening being generated as a result of too many deformations. In a preferred manner, the bone plate is additionally to provide the necessary stability in the load-carrying regions close to the fracture and is to be able to distribute the loads to several bone screws in the anchoring region. In addition, in a preferred manner the bone plate is to be as thin as possible and, in the region of the fracture or rather of the bridge, is to be provided with an outside contour which protects the soft tissue.

These and further objects are achieved, on the one hand, by a bone plate for the reconstruction or trauma treatment of a bone. In particular, this can be a human bone such as, for instance, a human mandible. As an alternative to this, the bones can also be, for example, talus, navicular, cuneiform, metatarsal I in the case of a medial column OP in the foot.

The bone plate includes a main portion with a first end and a second end, a first contact surface for contacting and fastening on a first region of the bone and a plurality of receiving means with in each case at least one in particular circular opening for receiving in each case at least one fastening element. The first region of the bone can be, for instance, the corpus of the mandible. If the bones to be treated are, as an alternative to this, the bones for a medial column OP in the foot, the first region can consist of one or several of the bones talus, navicular, cuneiform and metatarsal I. The named fastening element in a preferred manner is a bone screw.

At least two wings, which are arranged side by side, extend at least from the first end of the main portion. The wording "arranged side by side" means, in this connection, that the wings extend inside one and the same substantially planar surface or inside two substantially planar surfaces, the distance between them being smaller than the thickness of the wings, or that the wings are deformable at least in such a manner that they extend inside one and the same substantially planar surface or inside two substantially planar surfaces, the distance between them being smaller than the thickness of the wings—in particular in contrast to the wings shown in U.S. Pat. No. 4,726,808 which extend in planes which have a clearly larger distance between one another.

The wings, which extend from the first end of the main portion, extend in a preferred manner at an angle with respect to one another which is smaller than 90°, in a preferred manner smaller than 60° and in a particularly preferred manner smaller than 45°. Said angular ranges have proven to be advantageous in particular for the treatment of a human mandible.

The wings comprise in each case a second contact surface for contacting and fastening on a second region of the bone, and at least one receiving means with in each case at least one in particular circular opening for receiving in each case at least one fastening element. The second region of the bone can be, for example, the ascending ramus of a mandible, in particular an outside surface of said ascending ramus. If the bones, as an alternative to this, are the bones for a medial column OP in the foot, the second region can consist of one or several of the bones talus, navicular, cuneiform and metatarsal I. The receiving means of the wings can also be realized for receiving in each case at least one bone screw.

It is also within the framework of the invention that at least two wings, which are arranged side by side, extend not only from the first end, but that at least one wing or also at least two wings, which are arranged side by side and/or comprise the above-mentioned characteristics, also extend from the second end of the main portion.

The main portion and the at least two wings are realized in such a manner that the main portion has a first minimum bending rigidity, with reference to an axis which extends perpendicular to the first contact surface, and each of the at least two wings has a respective second minimum bending rigidity, with reference to an axis which extends perpendicular to the second contact surface. If the main portion or at least one of the wings is curved or if the main portion extends at an angle to at least one of the wings, the named perpendicular extending axes are not necessarily parallel to one another at different points of the contact surface of the main portion or of the wings. Here and below, it is always assumed that the axes extend locally perpendicular to the contact surface.

According to professional knowledge, the bending rigidity specifies the size of the bending torque in relation to the curvature produced as a result thereof. The bending rigidity for a homogeneous material is produced as a product from the modulus of elasticity of the material of the bone plate (in the region of the main portion or rather of one of the wings) and the axial geometrical moment of inertia with reference to a cross sectional plane which extends through the bone plate (that is to say through the main portion or rather through one of the wings).

Only the cross sectional planes which extend perpendicular to the respective contact surface, i.e. which extend parallel to an axis which extends perpendicular to the contact surface, are considered for the present invention. For calculating the axial geometrical moment of inertia with reference to such a cross sectional plane, a Cartesian system of coordinates is used, the origin of which is formed by the center of the area of said cross sectional surface and the x-axis of which extends perpendicular to the contact surface and, together with the z-axis, spans the cross sectional surface. The y-axis consequently extends perpendicular to the cross sectional surface and parallel to the contact surface. The axial geometrical moment of inertia can be determined arithmetically by the integral $$\int_A z^2 dA$$

of the squared z-coordinate over the cross sectional surface A. The bending rigidity according to the invention is produced in this way with reference to the x-axis which is perpendicular to the contact surface: when engaging a bending torque around the bending axis x, which is perpendicular to the contact surface, a curvature is effected about said bending axis x and consequently inside the contact surface.

Said bending rigidity obviously depends on the choice of the cross sectional plane, i.e. when referring to the system of coordinates introduced above, in particular on the choice of the y-axis and consequently also the z-axis, which, together with the x-axis which extends perpendicular to the contact surface, spans said cross sectional plane. The smallest bending rigidity with reference to a (local) axis which extends perpendicular to the first contact surface (when referring to the system of coordinates introduced above with reference to the local x-axis) which is produced from all the cross sectional planes which extend through the main portion and are perpendicular to the contact surface is regarded here and below as the first minimum bending rigidity (that is to say as minimum bending rigidity of the main portion), with reference to an axis which extends perpendicular to the first contact surface. The minimum bending rigidity of the wings is also understood in an analogous manner.

According to the invention, the first minimum bending rigidity (that is to say the minimum bending rigidity of the main portion) is greater than each of the second minimum bending rigidities (that is to say the minimum bending rigidities of the wings), but smaller than the minimum overall bending rigidity of all of the wings which extend from the first end. If at least two wings which are arranged side by side extend not only from the first end of the main portion, but at least two wings which are arranged side by side also extend from the second end of the main portion, the first minimum bending rigidity (that is to say the minimum bending rigidity of the main portion) can also be greater than that of the second minimum bending rigidities of the wings which extend from the second end of the main portion, but smaller than the minimum overall bending rigidity of all the wings which extend from the second end.

Analogously to the above definition, the minimum bending rigidity with reference to a (local) axis which extends perpendicular to the second contact surface and is produced from all the cross sectional planes which are perpendicular to the second contact surface is understood as the second minimum overall bending rigidity with reference to an axis which extends perpendicular to the second contact surface, wherein, however, only those cross sectional planes which extend through all the wings which extend from the first end are used for this purpose. A common coordinate center point is taken as the basis for calculating the overall bending rigidity and the geometrical moment of inertia. The minimum overall bending rigidity of the wings is therefore not to be equated with the sum of the minimum bending rigidities of the individual wings; for the minimum overall bending rigidity is greater than the sum of the minimum bending rigidities of the individual wings.

As has already been indicated above, the curvature of the bone plate produced by a bending torque is proportional to the engaged bending torque and reciprocally proportional to the bending rigidity. The largest curvature and consequently also the largest deformation are consequently generated in the region of the bone plate in which the bending rigidity is minimum.

The above-explained relations according to the invention lead to the following advantageous bending characteristics: in the initial state not yet fixed to the bone, the wings are bendable individually inside the plate plane by applying a comparatively small bending torque. As the first minimum bending rigidity is greater than that of the second minimum bending rigidities, in said initial state, the greatest deformation is effected in the region of the wings. Consequently, the wings can be deformed relatively simply inside the plate plane without the main portion being deformed in a considerable manner.

If the bone plate is fixed on the bone with the main portion and the wings in the implanted state, the wings are also fixed relatively to one another such that in said implanted state, the minimum overall bending rigidity is relevant. As this is greater than the first minimum bending rigidity, the wings can hardly ever be deformed inside the plate plane in the implanted state. If the bone to be treated is a mandible, the requirement that the overall bending rigidity is greater than the first bending rigidity is due to the real force distribution in the mandible: the load on the bone when chewing/biting is greater in the vicinity of the joint than toward the chin.

In contrast, the bending rigidity of the main portion, with reference to an axis which extends parallel to the contact surface and which determines the curvature of the main portion out of the plate plane (according to the above definition, that is to say in the case of a bend about the z-axis), is preferred to be smaller than the minimum bending rigidity of the main portion with reference to the axis which determines the curvature inside the plate plane (according to the above definition, that is to say in the case of a bend about the x-axis). The same also applies in an analogous manner to the wings. This makes it possible to bend the main portion or rather the wings out of the plate plane.

As has been shown, it is sufficient for adaptation to the majority of human mandibles when, with a corresponding design of the plate, the main portion of the bone plate is simply bent out of the plane defined by the contact surface (therefore, with reference to the above system of coordinates, as a result of bending about the z-axis), but not inside said plane (therefore, with reference to the above system of coordinates, about the x-axis). Bending inside the plane defined by the contact surface would additionally raise the risk of strain hardening.

The greatest differences between human mandibles consist instead in the angle at which the ascending ramus extends in relation to the corpus, in the height of the ascending ramus and in the length of the corpus. The wings provided for this purpose are not only bendable out of the plane defined by the contact surface, but are also slightly bendable inside the plate plane—at least insofar as they are not fastened on the mandible.

For determining whether a given bone plate meets the above-explained bending characteristics, it is not absolutely necessary to know the first minimum bending rigidity of the main portion, the second minimum bending rigidities of the wings and the minimum overall bending rigidity of the wings in a precise, numeric manner. Rather, it is sufficient for meeting the bending characteristics, that a first lower limit is known for the bending rigidities which is smaller than all the bending rigidities with reference to local axes which extend perpendicular to the first contact surface (referring to the above-introduced system of coordinates, with reference to the local x-axes) which are produced from the cross sectional planes which extend through the main portion and are perpendicular to the first contact surface;

that each of the wings, with reference to at least one cross sectional plane which extends through said wings and is perpendicular to the second contact surface, has a bending rigidity, with reference to a local axis which extends perpendicular to the second contact surface, which is smaller than the named first lower limit;

that a second lower limit for the overall bending rigidities is known which is smaller than all the overall bending rigidities with reference to local axes which extend perpendicular to the second contact surface and result from the cross sectional planes which are perpendicular to the second contact surface, wherein only those cross sectional planes which extend through all the wings which extend from the first end are used for this purpose;

that the main portion, with reference to at least one cross sectional plane which extends through the main portion and is perpendicular to the first contact surface, has a bending rigidity, with reference to a local axis which extends perpendicular to the first contact surface (referring to the above-introduced system of coordinates with reference to the local x-axis), which is smaller than the named second lower limit.

In order to reduce deformation of the main portion inside the contact surface as much as possible, the main portion can comprise a truss structure. This means that the main portion has struts which extend transversally with respect to a center line which runs from the first end to the second end of the main portion, that is to say perpendicular and/or parallel and/or in a preferred manner diagonally with respect to said center line. The receiving means advantageously form nodes of the truss structure, and the struts extend between said receiving means. However, truss structures where only individual or no receiving means form nodes are also conceivable.

It is conceivable and is within the framework of the invention that also at least one, in a preferred manner all the wings also include a truss structure as described above. In a preferred manner, however, at least one wing and, in a particularly preferred manner, each wing does not comprise any such truss structure. In this way, it can be achieved that at least in the non-implanted initial state, the wings are more easily deformable with reference to an axis which extends perpendicular to the respective contact surface than the main portion.

The main portion can be delimited at least on one side, in a preferred manner on both sides of at least one frame structure, which comprises an outer edge, which extends in a substantially rectilinear manner. The outer edge, in this case, is designated as substantially rectilinear when its minimum radius of curvature, at least on the longitudinal sides of the main portion, is greater than 10 mm and/or its width, measured perpendicular to the center line, along a length of 10 mm along the center line varies by no more than 2 mm. As a result, edges can be avoided, as are created, for example, by the ring-shaped screw receiving means of DE 103 35 281 A1 and which can be unpleasant for the patient and could even result in an injury to the body tissue. In the region of the first end and of the second end of the main portion and/also on the wings, the radius of curvature can, however, also be smaller or rather the width measured perpendicular to the center line can also vary more.

The main portion can have a width which is within the range of between 2 mm and 20 mm, in a preferred manner between 5 mm and 15 mm, in a particularly preferred manner between 8 mm and 10 mm. The length of the main portion, measured along a center line of the main portion, can be within the range of between 25 mm and 300 mm, in a preferred manner between 50 mm and 250 mm. At least one wing, in a preferred manner each wing, can comprise a length which is within the range of between 10 mm and 60 mm, in a preferred manner between 20 mm and 40 mm. In addition, at least one wing, in a preferred manner each wing, can comprise a width within the range of between 2 mm and 10 mm. Additionally, at least one wing, in a preferred manner each wing, can comprise a width which is at most 80% of the width of the main portion. Such dimensions and ratios, which can also be chosen independently of one another, are in any case suitable for human mandibles.

Perpendicular to the contact surfaces (that is to say to the first contact surface and to the second contact surface), the bone plate can comprise a thickness which is within the range of between 1 mm and 3 mm, in a preferred manner between 1 mm and 2 mm. On account of the bending characteristics according to the invention and/or of the truss structure, such small thicknesses nevertheless do not result in a loss in bending rigidity.

In a preferred manner, the bone plate is realized so as to be substantially planar. This means that both the main portion and the wings extend substantially in a common plane (apart from the extent of the bone plate on account of its above-mentioned thickness). The above bone plate from U.S. Pat. No. 4,726,808 is not planar according to said definition as its two wings extend in different planes. A substantially planar bone plate is simpler to produce than a bone plate which has already been adapted to the anatomical form. In addition, a substantially planar form facilitates the transport and storage of the bone plate.

In addition, the main portion, in a preferred manner, is deformable out of the plane defined by the contact surface into an anatomical form in which it is fastenable on at least part of an in particular human mandible substantially only as a result of bending. In other words, the main portion is realized in such a manner that it does not need to be bent or only needs to be bent at most insignificantly about the axis which extends perpendicular to the contact surface in order to be transferred into the anatomical form. Bendability is largely to be reduced according to the invention, as has been explained above, so that, also in the implanted state, the bone plate is deformable at most slightly by means of forces or bending torques which act inside the named plane.

The bone plate consists in a preferred manner of a biocompatible implant material, such as, for example, titanium and its alloys, implant steel, implantable plastics material or implantable ceramic.

In many situations, it is advantageous when a bone screw, through corresponding design of both a blocking element of the bone screw, in particular of the screw head, and of the plate opening, can be fixed at different angles relative to the bone plate. These types of structures at screw heads and plate openings are disclosed, for example, in International Patent Application WO 2004/086990. The plate openings disclosed there, however, only allow the blocking element, in particular the screw head, to be fixed at a variable angle when the screw is inserted through the openings from a predefined top surface of the bone plate in the direction of a predefined oppositely situated bottom surface of the bone plate; variable angle fixing in a direction opposite to this is not possible. This can restrict the usefulness of the bone plate for many applications.

A further object of the present invention is to develop the bone plates disclosed in the prior art and in particular the openings thereof further in such a manner that bone screws which are suitable for this purpose (in particular the bone screws disclosed in WO 2004/086990) are able to be fixed on the bone plate at a variable angle in both directions.

This and further objects are achieved by a bone plate with at least one opening for receiving in each case at least one bone screw. In particular, this can be a bone plate as described above for the reconstruction or trauma treatment of an in particular human bone, such as, for instance, an in particular human mandible.

The opening penetrates the bone plate along a longitudinal axis from a top surface of the bone plate to an oppositely situated bottom surface of the bone plate. On the top surface the opening opens out into a first receiving region which is realized for the receiving and in particular angularly-variable fixing of a blocking element of a bone screw in a first direction.

According to the invention, on the bottom surface the opening opens out into a second receiving region which is realized for the receiving and in particular angularly-variable fixing of the blocking element in a second direction. In this case, the second direction is substantially opposite the first direction. This means, here and below, that the blocking element can be received and fixed in the first receiving region in such a manner that the bone screw passes through the bone plate from the top surface in the direction of the bottom surface, and the blocking element can be received and fixed in the second receiving region in such a manner that the bone screw passes through the bone plate from the bottom surface in the direction of the top surface.

In a preferred manner, the first receiving region is delimited by a first inside wall and the second receiving region is delimited by a second inside wall, wherein in each case at least one recess is formed both in the first inside wall and in the second inside wall and in each of said recesses the distance away from the respective inside wall increases in dependence on the angle of rotation about the longitudinal axis. In an even more preferred manner, both the first inside wall and the second inside wall are realized in an at least approximately spherical, paraboloid, ellipsoid or hyperboloid manner in the region of each of the respective recesses.

In other words, the opening therefore includes, in a preferred manner, an inside wall both in the region of the top surface of the bone plate and in the region of the bottom surface of the bone plate, said inside wall being provided in each case as disclosed in WO 2004/086990.

The first and the second receiving regions of the opening can be realized independently of one another for right-rotating blocking or for left-rotating blocking. In this case, right-rotating blocking, for example, for the first receiving region means that the blocking element of the bone screw, when viewed in a viewing direction from the top surface of the bone plate to the bottom surface of the bone plate, is fixable in the first receiving region as a result of rotating the bone screw clockwise. In an analogous manner, left-rotating blocking, for example, for the second receiving region, means that the blocking element, when viewed in a viewing direction from the top surface of the bone plate to the bottom surface of the bone plate, is fixable in the first receiving region as a result of rotating the bone screw anticlockwise.

In a preferred manner, the first and the second receiving regions of the opening are realized for same-direction blocking. This means that either both receiving regions are realized for right-rotating blocking or both receiving regions are realized for left-rotating blocking.

Said design allows a correspondingly designed bone screw to be both inserted though the opening from the top surface in the direction of the bottom surface and fixed at a variable angle in this manner and to be inserted through the opening from the bottom surface in the direction of the top surface and to be fixed at a variable angle in this manner. This makes it possible to design bone plates, in particular the above-described bone plates, in such a manner that either the bottom surface or the top surface can be contacted onto the bone. In particular, one and the same bone plate can be used either for a left-sided or for a right-sided defect. In this manner, even fewer different bone plates are necessary in order to allow for individual adaptation, which simplifies storage even more. The bone plate even allows for some applications where at least one first bone screw can be inserted through a first opening from the top surface in the direction of the bottom surface and at least one second bone screw can be inserted through a second opening from the bottom surface in the direction of the top surface in one and the same bone plate and can be fixed at a variable angle.

The first and/or the second inside wall can comprise, independently of one another, one, several or all the features disclosed in WO 2004/086990. The disclosure in this respect in WO 2004/086990 is hereby expressly incorporated into the present application.

In particular, the inside wall can comprise at least three or even precisely three recesses which are distributed uniformly along its circumference and widen outward in each case in a wedge-shaped manner away from the longitudinal axis of the receiving means; and/or the receiving region can be provided with an in particular spherical depression for receiving, for example, a screw head with a spherical head underside.

A further aspect of the invention relates to a surgical set which includes at least one bone plate as described above having at least one opening with two receiving regions as well as at least one bone screw with a screw shank and a blocking element, in particular a screw head which protrudes outward above the screw shank and a thread of the screw shank. In this case, the blocking element is receivable electively in the first receiving region or in the second receiving region of the opening of the bone plate and is fixable in particular at a variable angle.

In a preferred manner, the blocking element, in particular the screw head, is provided with a circumferential outside surface which extends substantially in the direction of a longitudinal axis of the bone screw and comprises at least one clamping surface which—when viewed in an azimuth plane perpendicular to the longitudinal axis—widens outward in a wedge-shaped manner away from the longitudinal axis. In a preferred manner, the circumferential outside surface of the blocking element is realized in an at least approximately spherical, paraboloid, ellipsoid or hyperboloid manner at least in the region of the clamping surface.

In other words, the bone screw is realized in a preferred manner in the manner in which it is disclosed in WO 2004/086990.

A bone screw designed in such a manner allows for elective insertion into the opening of the bone plate in directions which are substantially opposite one another, as has already been explained above. The bone screw can also comprise one, several or all of the features disclosed in WO 2004/086990; the disclosure in this respect in WO 2004/086990 is also hereby expressly incorporated into the present application. In particular, the outside surface can comprise at least three or even precisely three clamping surfaces which are distributed uniformly along its circumference and widen outward in each case in a wedge-shaped manner away from the longitudinal axis.

Yet another aspect of the invention relates to a reconstruction set for the reconstruction of an in particular human mandible, the reconstruction set comprising at least one bone plate as described above as well as at least one of the following further elements:
 at least one connecting plate which comprises means for connecting to at least one of the bone plates or to part of one of the bone plates, in particular at least one opening for receiving a fastening element, in particular a connecting screw or a bone screw,
 at least one mandibular joint prosthesis and, as an option, at least one carrier element for holding the mandibular joint prosthesis, wherein the mandibular joint prosthesis and/or the carrier element comprises means for connecting to at least one wing, in a preferred manner to all the wings which extend from the first end of the main portion of the bone plate, in particular at least one opening for receiving a fastening element, in particular a connecting screw or a bone screw.

Such a reconstruction set only requires a comparatively small number of different elements with which, however, nevertheless, a large part of the defects in human mandibles can be treated, as will be explained again below in conjunction with FIGS. 9a-i and 10.

As an option, the reconstruction set can also include further bone plates which are not according to the invention—that is to say, for example, bone plates with a main portion, from the ends of which in each case only one wing or no wing at all extends.

Said connecting plates can comprise, in at least one end region, two openings which are movable at the same time to coincide with at least two corresponding openings of at least one of the bone plates or of at least part of one of the bone plates. For connection, a fastening element, which is realized as a connecting screw, can pass through one of the openings of a bone plate, and an external thread of the connecting screw can enter into an internal thread which is situated in the connecting plate.

The invention is explained in detail below by way of several exemplary embodiments, in which:

FIG. 1: shows a panoramic X-ray view of a human mandible with a first bone plate according to the invention fastened thereon;

FIG. 2: shows a panoramic X-ray view of a human mandible with a second bone plate according to the invention fastened thereon;

FIG. 3a: shows a panoramic X-ray view of a human mandible with a third bone plate according to the invention fastened thereon;

FIG. 3b: shows a perspective sectional view along the cutting line marked in FIG. 3a;

FIG. 4a: shows a perspective view of the second bone plate according to the invention according to FIG. 2;

FIG. 4b: shows a perspective view of a detail of the second bone plate according to the invention;

FIG. 5a: shows a top view of the second bone plate according to the invention;

FIG. 5b: shows a sectional view of the second bone plate according to the invention along the cutting line E-E shown in FIG. 5a;

FIG. 6a: shows a perspective view of a first bone screw of a surgical set according to the invention;

FIG. 6b: shows a top view of the first bone screw of a surgical set according to the invention;

FIG. 7: shows two views of a first reconstruction set according to the invention with a first bone plate according to the invention, a second bone plate according to the invention and a connecting plate;

FIG. 8: shows a second reconstruction set according to the invention with three bone plates according to the invention, a bone plate which is not according to the invention, a connecting plate, a right and a left mandibular joint prosthesis, a carrier element for holding one of the mandibular joint prostheses, four connecting screws for connecting the mandibular joint prostheses to the carrier element, four connecting screws for electively connecting one of the bone plates to the carrier element or to the connecting plate and one mandibular joint stabilizing element;

FIGS. 9a-i: show nine panoramic X-ray views of human mandibles with diverse defects and elements of the reconstruction set according to FIG. 8;

FIG. 10: shows a further overview of human mandibles with diverse defects and elements of the reconstruction set according to FIG. 8;

FIGS. 11a and b: show two views of a second bone screw with a screw head and a blocking element arranged at the tip;

FIGS. 12a and b: show two views of a third bone screw without a screw head, but with a blocking element arranged at the tip;

FIGS. 13a to c: show three perspective views of a surgical set according to the invention with a bone plate according to the invention and four bone screws;

FIG. 14a: shows a perspective view of a bone plate according to the invention without bone screws;

FIG. 14b: shows a perspective view of the bone plate according to the invention according to FIG. 14a with four bone screws inserted therein;

FIGS. 15a to c: show three views of a detail of a further bone plate with an opening with two receiving regions;

FIGS. 16a to c: show three views of a detail of yet another bone plate with an opening with two receiving regions;

FIGS. 17a to c: show three views of a detail of yet another bone plate with an opening with two receiving regions;

FIGS. 18a to c: show three views of a detail of yet another bone plate with an opening with two receiving regions.

FIG. 1 shows a human mandible 113 with a corpus 142 and two ascending ramuses 112. For clearer representation, a projection similar to a dental panoramic X-ray view has been chosen where the outside surface of the mandible 113 has been shifted to the drawing plane. A first bone plate 101 according to the invention is contacted and fastened on the mandible 113. The bone plate 101 includes a main portion 109 which has a first end 143 and an oppositely situated second end 148 and extends along a center line M from the first end 143 to the second end 148. The main portion 109 additionally has a first contact surface 141 which cannot be seen here and on which the main portion 109 is contacted and fastened on the corpus 142 (see FIG. 4a in this respect). In addition, the main portion 109 has a plurality of receiving means 108, 108' with in each case a circular opening 102, 102' for receiving in each case one bone screw 301 which is not shown here (see FIGS. 6a and 6b in this respect).

Two wings 110, which are arranged side by side, extend from both the first end 143 and from the second end 148 of the main portion 109. Said wings have in each case a second contact surface 144, which is not shown here (see FIG. 4a also in this respect), for contacting and fastening on an outside surface of one of the ascending ramuses 112. In addition, the wings 110 have receiving means 145 with, in each case, one circular opening 146 for receiving, in each case, one bone screw 301 which is not shown here (see FIGS. 6a and 6b in this respect).

The main portion 109 comprises a first minimum bending rigidity in a cross sectional plane, which is not shown here (see FIG. 3b for the representation of a cross sectional plane of another bone plate), with reference to an axis which extends perpendicular to the first contact surface 141 (and consequently also perpendicular to the drawing plane). Each wing 110 comprises a respective second minimum bending rigidity in respective cross sectional planes, which are also not shown here, with reference to axes which extend perpendicular to the respective second contact surface 144 (and consequently also perpendicular to the drawing plane). In this case, according to the invention, the first minimum bending rigidity is greater than each of the second minimum bending rigidities, but smaller than the minimum overall bending rigidity of all the wings 110 which extend from the first end 143 and also smaller than the minimum overall bending rigidity of all of the wings 110 which extend from the second end 148.

The main portion 109 comprises a truss structure. Namely, it has struts 104 which extend transversally with respect to the center line M. The openings 102 are arranged on a first side of the center line M, and the openings 102' are arranged on a side of the center line M which is situated opposite the first side. The receiving means 108, 108' with the circular openings 102, 102' are arranged here at the nodes of the truss structure. As an alternative to this, however, nodes without screw holes are also conceivable. In the exemplary embodiment shown here, the wings 110 do not comprise any such truss structure.

Proceeding from the named bending characteristics and the truss structure, the advantages of the bone plate 101 according to the invention, which have already been explained in detail above, are as follows:

In the initial state, in particular in the delivery state, the bone plate 101 can be substantially planar, which simplifies production, transport and storage. In order to be able to mold the bone plate 101 to the individual anatomy of a patient, substantially only the wings 110, not however also the main portion 109, are able to be bent as a result of suitably chosen bending torques inside the plate plane. As a result, substantially only the wings 110 in the plate plane can be molded to the individual anatomy of a patient, for example to the angle between corpus 142 and rising ramus 112. The main portion 109 can only be deformed into an anatomical form in which it can be fastened on the mandible 113 substantially by bending out of the plane defined by the contact surface 141.

As has been shown in studies, where there is suitable shaping of the bone plates, deforming the main portion 109 inside the plate plane is also not even necessary in order to be able to mold the bone plate 101 to the corpus 142 of a plurality of human mandibles 113. Instead, the advantage of the slight deformability of the main portion 109 inside the plate plane is that the bone plate 101 is stable in relation to forces and bending torques acting in said plate plane.

If the bone plate 101 is then fastened to the mandible 113, the two wings 110 are also fixed relatively to one another such that the minimum overall bending rigidity of said wings 110 in said implanted state is relevant. As said overall bending rigidity is greater than the first minimum bending rigidity of the main portion 109, even the wings 110 are hardly able to be deformed inside the plate plane in the implanted state, which also results in greater stability in said region in relation to forces and bending torques acting in the plate plane. If the bone to be treated is a mandible, the requirement that the overall bending rigidity is greater than the first bending rigidity is due to the real force distribution in the mandible: the load on the bone when chewing/biting is greater in the vicinity of the joint than toward the chin.

The main portion 109 is delimited on both sides $S_1$, $S_2$ by a frame structure 105, which comprises an outer edge 107, which extends in a substantially rectilinear manner. As a result, it is possible to avoid edges which could result, for example, in injuries to the body tissue.

The main portion 109 has a width $b_1$ of 10 mm and a length $l_1$, measured along the center line M, of 145 mm. The wings 110 have a width $b_2$ of 7 mm. The shorter wings 110 shown in the upper position in FIG. 1 have a length $l_2$ of 19 mm, and the longer wings 110 shown in the bottom position in FIG. 1 have a length $l_2'$ of 26 mm. Consequently, each wing 110 comprises a width $b_2$ which is at most 80% of the width $b_1$ of the main portion 109.

The bone plate consists of a biocompatible implant material, such as, for example, titanium and its alloys, implant steel, implantable plastics material or implantable ceramic.

FIGS. 2 and 3a show a human mandible 113 with two further bone plates 101' and 101", respectively, according to the invention. The main portions 109 thereof comprise two wings 110 in each case only on a first end 143. In each case, only one single wing 110 is arranged on the oppositely situated second end 148. The main portion 109 of the third bone plate 101" according to the invention shown in FIG. 3a is longer than the main portion 109 of the second bone plate 101' according to the invention shown in FIG. 2. Consequently, the third bone plate 101 according to the invention shown in FIG. 3a is able to cover a larger region of the corpus 142, as will be made clear again below in conjunction with FIGS. 9a to 9i and 10.

FIG. 3b shows a cross sectional view along the cutting line in FIG. 3a. The cross sectional plane extends perpendicular to the center line M of the main portion 109. It is, however, not necessarily the one at which the minimum bending rigidity of the main portion 109 is present. Marked is a Cartesian coordinate system, the origin of which is formed by the common center P of the area of the three part cross sectional surfaces $A_1$, $A_2$ and $A_3$. The x-axis is perpendicular to the contact surface 141, and the y-axis extends substantially parallel to the center line M. The x-axis and the z-axis together span the part cross sectional surfaces $A_1$, $A_2$ and $A_3$. The axial geometrical moment of inertia can be determined arithmetically by the integral $$\int_A z^2 dA = \int_{A_1} z^2 dA + \int_{A_2} z^2 dA + \int_{A_3} z^2 dA$$

of the squared z-coordinate over the cross sectional surface A which is composed of the three part cross sectional surfaces $A_1$, $A_2$ and $A_3$. For each of the three integrals, in this case, a common coordinate system is used, the coordinate origin being in the center of the overall surface and not in the centers of the surfaces of the part cross sectional surfaces. The bending rigidity is produced as a product of said axial geometrical moment of inertia with the modus of elasticity of the bone plate 101". As has been explained above, it is not, however, absolutely necessary for determining whether the bone plate 101" meets the above-explained bending characteristics according to the invention to know the first minimum bending rigidity of the main portion 109, the second minimum bending rigidities of the wings 110 and the minimum overall bending rigidity of the wings 110 in a precise, numerical manner.

FIG. 4a shows a perspective view of the second bone plate 101' according to the invention according to FIG. 2. The main portion 109 has a first contact surface 141 for contacting and fastening on the corpus 142, and the two wings 110 include in each case a second contact surface 144 for contacting and fastening on the ascending ramus 112.

Each of the openings 102, 102' and 146 has a structure which can be seen in the view of a detail according to FIG. 4b. The opening 102 serves for receiving a first bone screw 301 which is shown in FIGS. 6a and 6b. The opening 102 passes through the bone plate 101 along a longitudinal axis L from a top surface 202 of the bone plate 101 to an oppositely situated bottom surface 203 of the bone plate 101. On the top surface 202, the opening 102 opens out into a first receiving region 204 which is delimited by a first inside wall 205. On the bottom surface 203, the opening 102 opens out into a second receiving region 206 which is delimited by a second inside wall 207.

Three recesses 208 are formed in the circumferential direction in the first inside wall 205. In each of said three recesses 208, the distance to the first inside wall 205 increases in dependence on the angle of rotation about the longitudinal axis L. In addition, in the exemplary embodiment shown here, the first inside wall 205 is realized in a spherical manner in the region of each of the recesses 208. As an alternative to this, however, the first inside wall 205 can also be realized, for example, in a paraboloid, ellipsoid or hyperboloid manner. In an analogous manner, three recesses 209 are formed in the circumferential direction in the second inside wall 207. In each of said three recesses 209, the distance to the second inside wall 207 increases in dependence on the angle of rotation about the longitudinal axis L. In addition, in the exemplary embodiment shown here, the second inside wall 207 is realized in a spherical manner in the region of each of the recesses 209, but, as an alternative to this, could also be realized, for example, in a paraboloid, ellipsoid or hyperboloid manner. The first receiving region 204 also includes a spherical depression 210 for receiving a connecting element, in particular a screw head, of a bone screw which is not shown here. In addition, the first recess 204 has an outlet contour 212 which serves for removing a bone screw.

The two receiving regions 204, 206 are realized for a blocking means which rotates in the same direction. More precisely, both receiving regions 204, 206 are realized for a right-rotating blocking means. A blocking element of a bone screw can therefore be fixed both in the first receiving means 204 in the direction of view from the top surface 202 to the bottom surface 203 by rotating the bone screw clockwise and can be fixed in the second receiving region 206 in the direction of view from the bottom surface 203 to the top surface 202 by rotating the bone screw anticlockwise.

FIG. 5a shows a top view of the second bone plate 101' according to the invention. As can be seen in the sectional view according to FIG. 5b, the second receiving region 206 also includes a spherical depression 211 and an outlet contour 213.

FIGS. 6a and 6b show a first bone screw 301 which can be inserted at a variable angle in each of the openings 102, 102' and 146. Said bone screw 301 is identical to the one disclosed in WO 2004/086990. It comprises a screw shank 320 with a thread 321 as well as a screw head 310 which is realized as a blocking element and protrudes outward above the screw shank 320 and the thread 321. The screw head 310 comprises an engagement contour 311 in which, for example, a screwdriver can be inserted in order to insert or remove the bone screw 301. In addition, the screw head 310 is provided with a circumferential outside surface which extends substantially in the direction of a longitudinal axis K of the bone screw 301 and comprises three clamping surfaces 330 which are distributed uniformly in the circumferential direction. When viewed in an azimuth plane perpendicular to the longitudinal axis K, the clamping surfaces 330 widen outward in a wedge-shaped manner and away from the longitudinal axis K. The outside surface is realized in a spherical manner in the region of the clamping surface 330. Said clamping surfaces 330 make it possible for the screw head 310 to be able to be blocked electively with the first inside wall 205 or the second inside wall 207, just as is described in detail in WO 2004/086990 (which simply discloses, however, an opening with one single receiving region as disclosed here).

In this way, the bone screw 301 is able to be inserted both through the opening 102 from the top surface 202 in the direction of the bottom surface 203 and be fixed in this manner at a variable angle on the bone plate and inserted through the opening 102 from the bottom surface 203 in the direction of the top surface 202 and be fixed in this manner at a variable angle on the bone plate. Consequently, both the top surface 202 and the bottom surface 203 can serve electively as contact surfaces which are contacted onto the bone. The bone plates can consequently be used electively and according to requirement for left-sided or right-sided defects without having to dispense with fixing at a variable angle. This clearly reduces the range of bone plates to be held ready.

The reconstruction set according to the invention shown in FIG. 7 includes the two bone plates 101' and 101" according to the invention shown in FIGS. 2 to 3b as well as a connecting plate 131 which is shown here twice in two different views. As means for connecting to a bone plate, for example one of the bone plates described above, the connecting plate 131 includes several openings 132 for receiving a fastening element, such as, for example, a connecting screw 163 which is shown in FIG. 8. For connection, the connecting screw 163 can pass through one of the openings 102, 102' or 146 of the bone plates according to the invention or also an opening in another bone plate, and its thread can engage a thread which is situated in the connecting plate. This allows for variable lengthening or even for coupling between two plates for adapting to the individual anatomy or rather to the individual bone defect.

FIG. 8 shows a second reconstruction set according to the invention. This includes

- the bone plates 101, 101' and 101" according to the invention according to FIGS. 1 to 3b;
- a bone plate 101''' which is not according to the invention and only has one single wing 110 at each end of the main portion 109;
- a connecting plate 131 as reproduced in FIG. 7;
- one mandibular joint prosthesis 160 each for the left and the right side;
- a carrier element 161 for holding and height-variable adjusting of one of the mandibular joint prostheses 160 and for fastening on a bone plate or for directly fastening on the bone (as an alternative to this, the reconstruction set can also include several carrier elements 161);
- connecting screws 162 (four screws in the exemplary embodiment shown here) for connection of one of the mandibular joint prostheses 160 to the carrier element 161;
- connecting screws 163 (four screws in the exemplary embodiment shown here) for connection of the carrier element 161 to one of the wings 110 or for connection of the connecting plate 131 to one of the bone plates;
- a mandibular joint stabilizing element 164 for cross connection of two wings 110 by means of connecting screws 163 (as an alternative to this, the reconstruction set can also include several mandibular joint stabilizing elements 164).

FIGS. 9a to 9i show how the reconstruction set according to FIG. 8 can be used for a plurality of bone defects:

According to FIGS. 9a and 9b, smaller bone defects can be treated by means of the shorter bone plate 101'.

FIG. 9c shows how a larger defect can be treated using the longer bone plate 101".

A mandibular joint can also be replaced by means of a shortened bone plate 101", the carrier element 161, a mandibular joint prosthesis 160 and a mandibular joint stabilizing element 164 as well as the associated connecting screws 162 and 163, as shown in FIG. 9d.

Figure 9A:
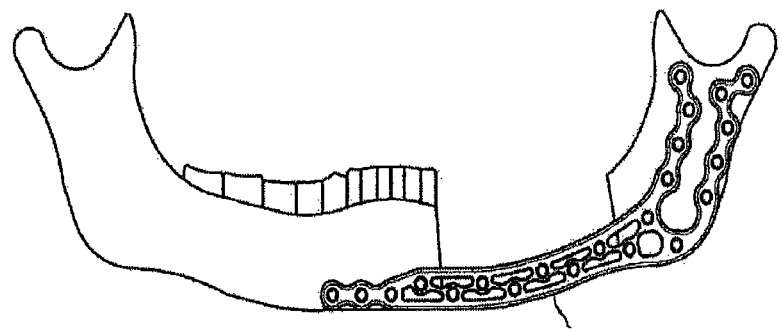
FIG. 9e shows the use of the bone plate 101 for a large central defect.
FIG. 9f shows once again a use of the bone plate 101' where the defect is even larger than in FIGS. 9a and 9b.
Figure 9B:
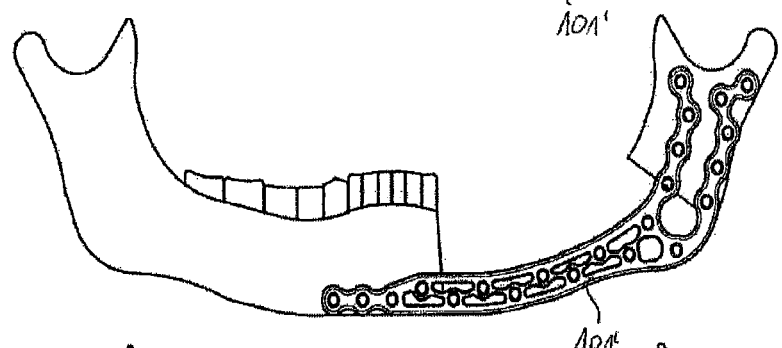
Figure 9C:
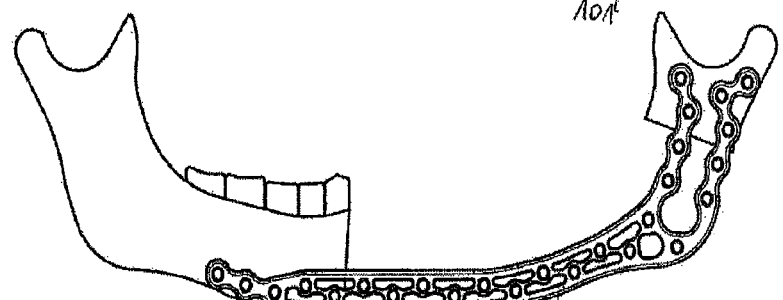
Figure 9D:
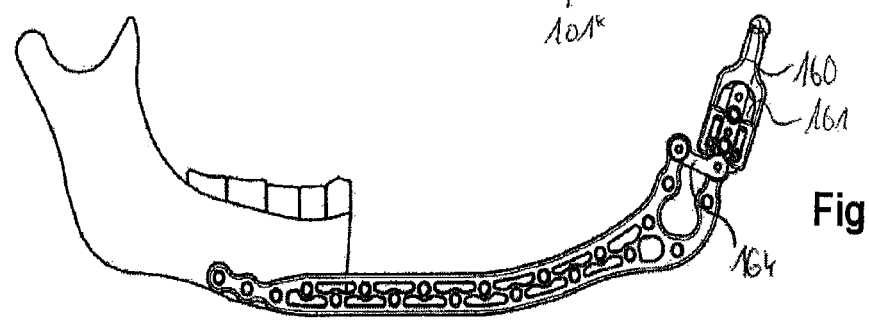
Figure 9E:
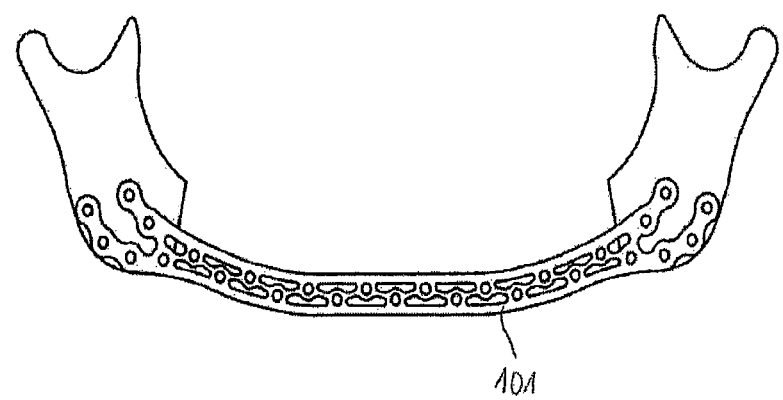
Figure 9F:
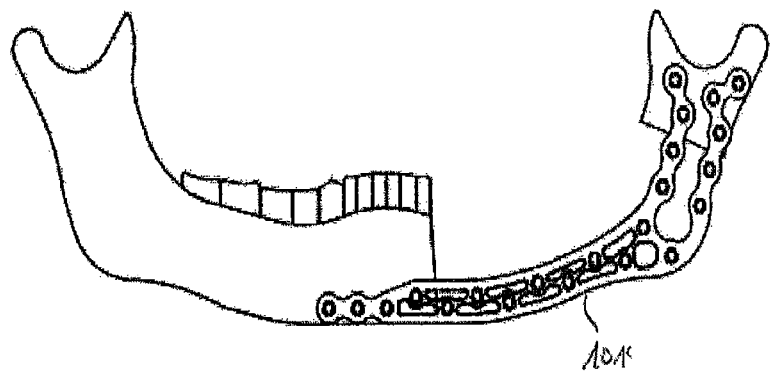
Figure 9G:
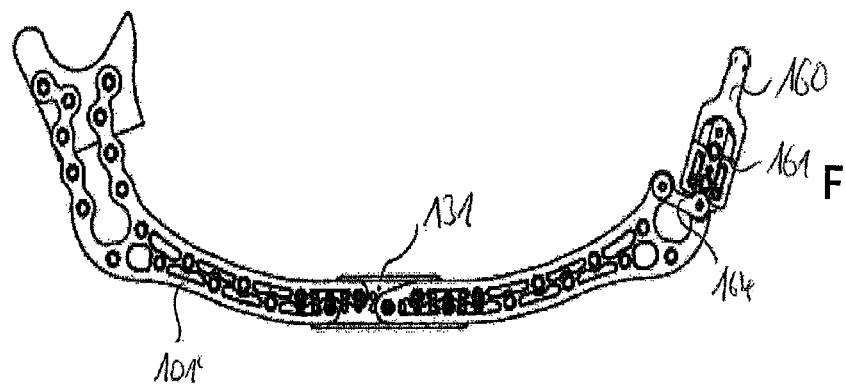

In the situation according to FIG. 9g, two bone plates 101' and 101", which have been connected by means of the connecting plate 131, have been used. Whilst the bone plate 101' has been trimmed in the region of the chin, this has been effected in the case of the bone plate 101" in the region of the chin and of the ascending ramus. In addition, a mandibular joint prosthesis 160, the carrier element 161 and the mandibular joint stabilizing element 164 with the associated connecting screws 162 and 163 have also been used here.

Figure 9H:
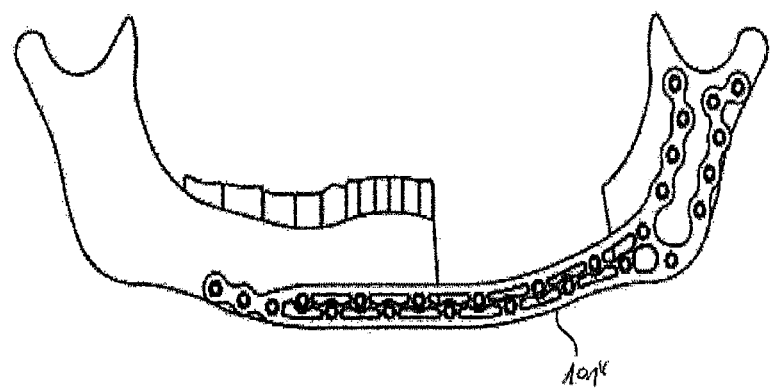

FIG. 9h once again shows a use of the longer bone plate 101".

Figure 9I:
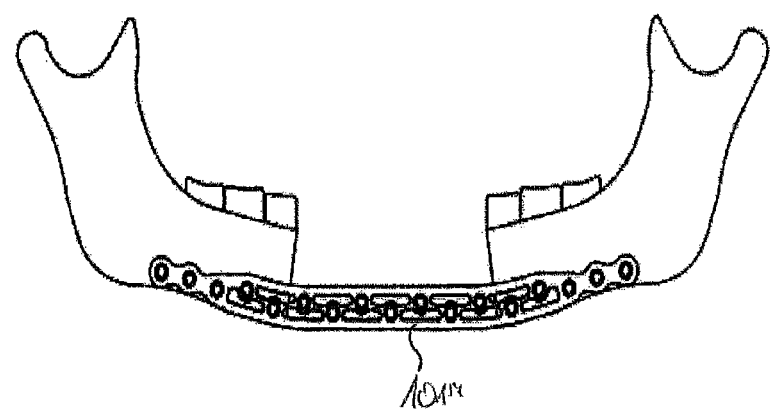

The use of the bone plate 101''' can be seen finally in FIG. 9i.

As an alternative to this, however, a reconstruction set is also conceivable and is within the framework of the invention where a mandibular joint prosthesis can be connected directly, that is to say without an additional carrier element, to one of the bone plates.

Figure 10:
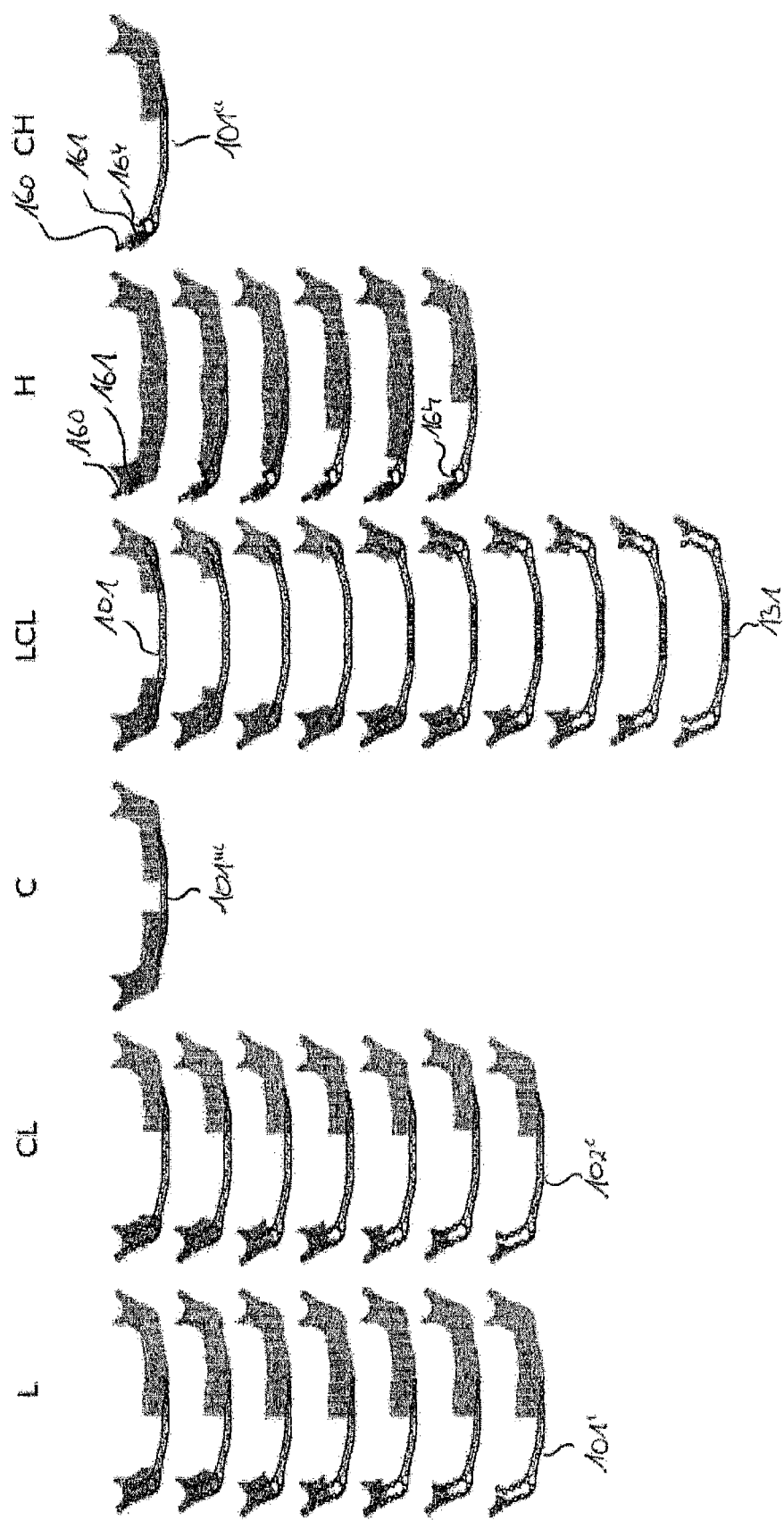

FIG. 10 once again shows an overview of a plurality of bone defects according to the conventional HCL classification:

The L defects (lateral continuity defects) can be treated with the shorter bone plate 101' which has two wings only at one end. Only defects on the right side of the patient are shown, the analogous application of the same bone plate 101' on the left side of the patient is also possible on account of the above-described double receiving regions of the openings.

The longer bone plate 102' which also includes two wings only on one end, can be used for CL defects (lateral and central continuity defects). Only defects on the right side of the patient are shown, the analogous application of the same bone plate 102' on the left side of the patient is also possible on account of the above-described double receiving regions of the openings.

C defects (central continuity defects) can be treated using the bone plate 101''' which, in the realization shown here, does not have any wings on either of the two ends. Plates for C defects with two wings on one side or on both sides are, however, conceivable.

For the treatment of LCL defects (double lateral and central continuity defects), the bone plate 101 (top four representations) or the bone plates 101' or 101" can be used together with the connecting plate 131 (bottom six representations).

For H defects (hemi-mandibular continuity defects), it is possible to use either only one mandibular joint prostheses 160 with carrier element 161 or additionally the mandibular joint stabilizing element 164 and one of the bone plates. In the case of the application shown at the very top in column "H", no bone plate is inserted; instead of which the carrier element 161 is fastened directly on the bone. Here too, only the use on the right side of the patient is shown (see above).

For CH defects (hemi-mandibular and central continuity defects), a combination of bone plate 101" trimmed to the wings 110, mandibular joint stabilizing element 164, carrier element 161 and mandibular joint prostheses 160 can be used. Here too, only the use on the right side of the patient is shown (see above).

All in all, it is shown that all bone defects can be treated with a comparatively small reconstruction set. This is brought about, among other things, by the ability to use both sides of the bone plates which is traced back to the double receiving regions according to the invention of the openings.

Figure 11A:
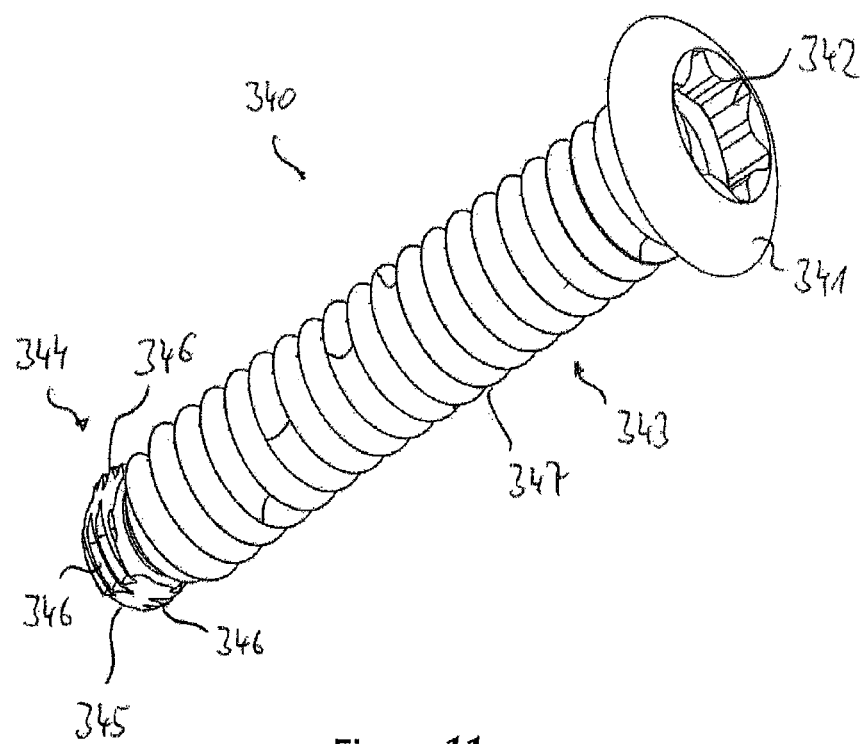
Figure 11B:
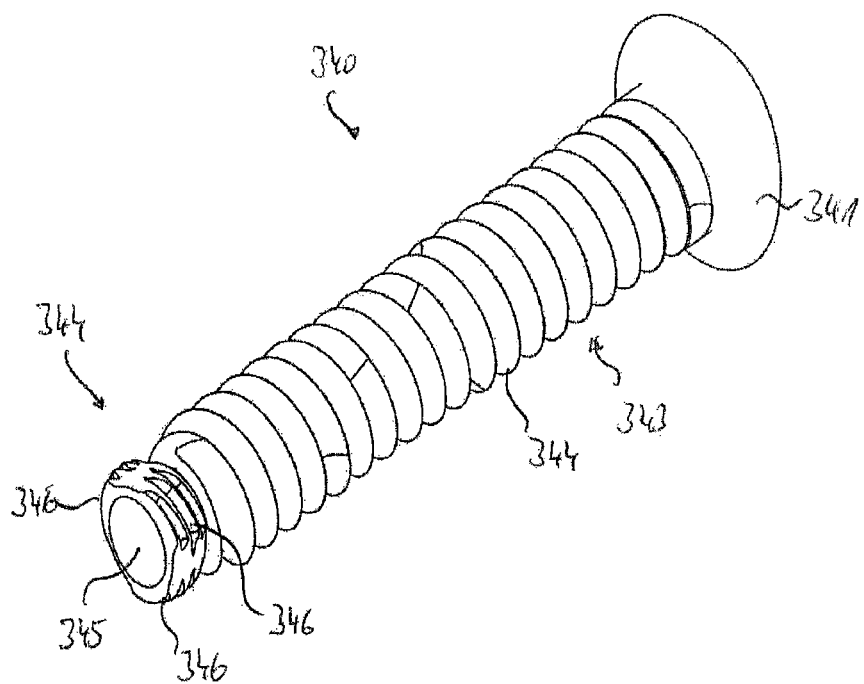

FIGS. 11a and 11b show a second bone screw 340. This includes a screw head 341 with an engagement contour 342, a screw shank 343 with a thread 347 and a blocking element 345 which is arranged on an end 344 of the bone screw 340 which is situated opposite the screw head 341. Said blocking element 345 includes three clamping surfaces 346 which are distributed uniformly in the circumferential direction and are realized as disclosed in WO 2004/086990.

Figure 12A:
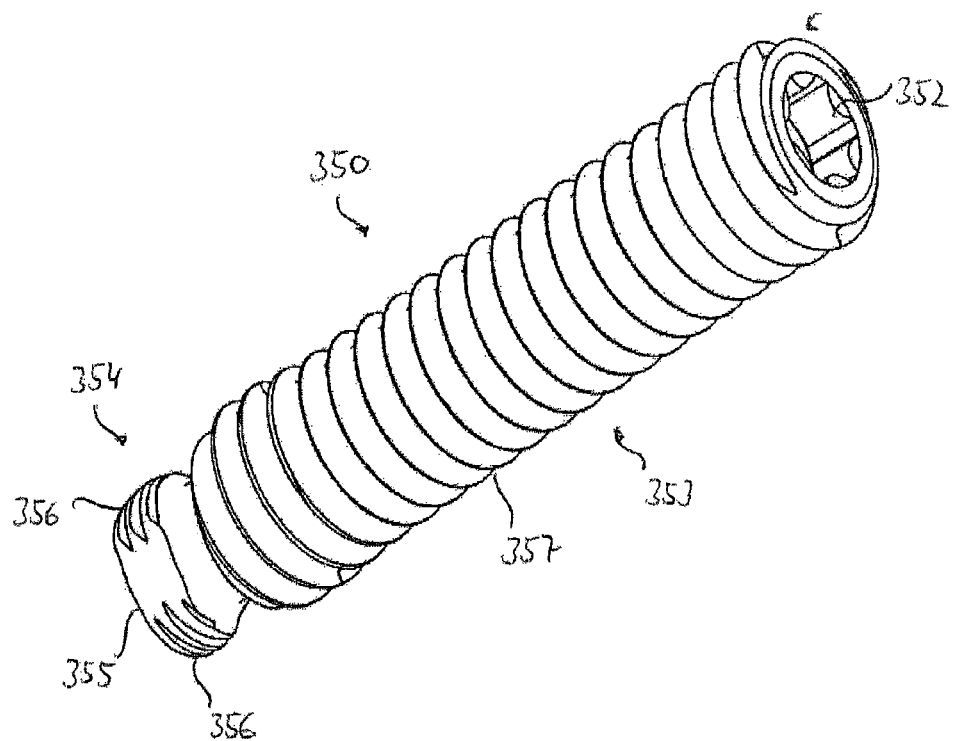
Figure 12B:
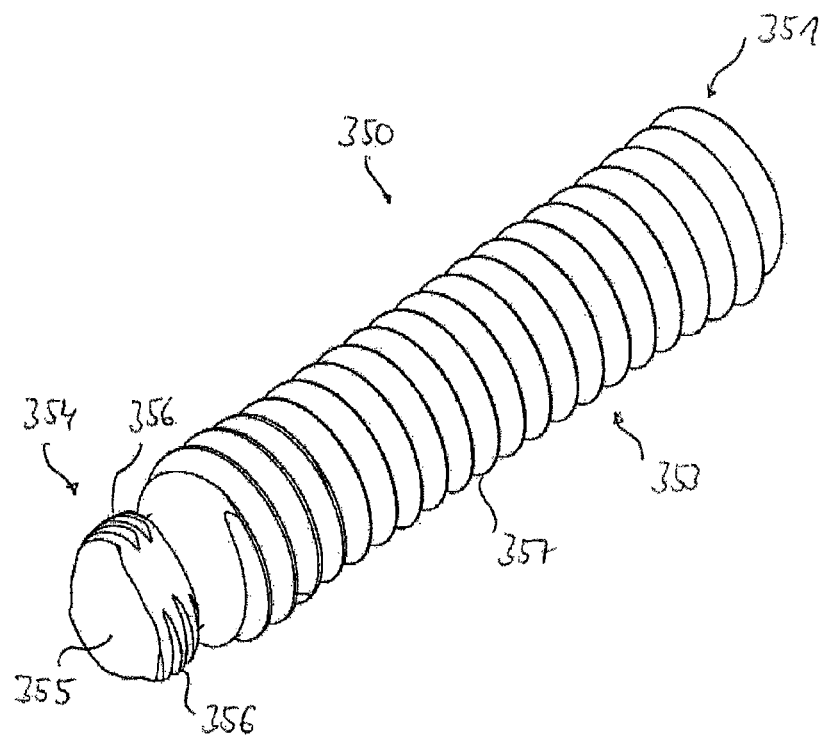

FIGS. 12a and 12b show a third bone screw 350 which, however, does not comprise a screw head. On a first end 351 it has an engagement contour 352 and on a second end 354 which is situated opposite the first end 351 it comprises a blocking element 355 which has three clamping surfaces 356 just as the blocking element 345 shown in FIGS. 11a and 11b. A screw shank 353 with a thread 357 extends between the first end 351 and the second end 354.

Figure 1:
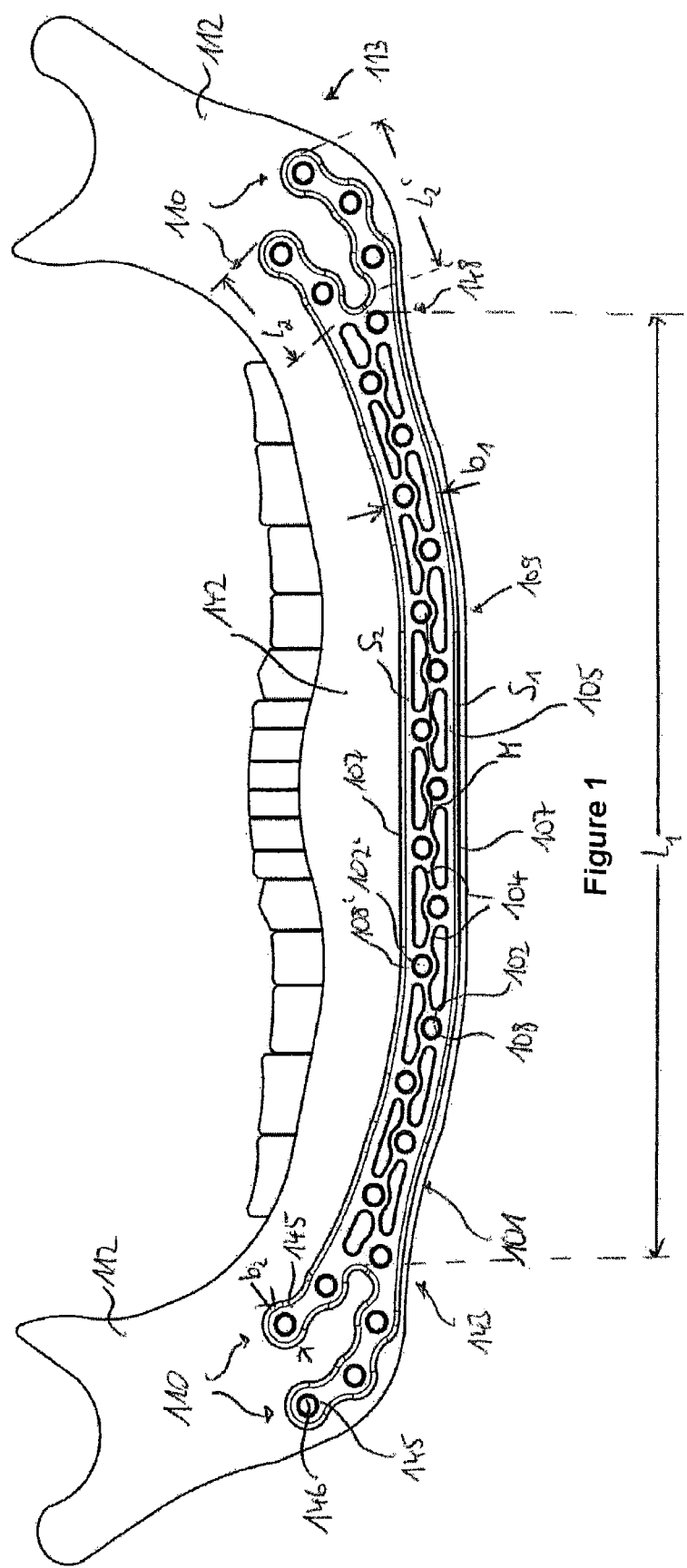
Figure 2:
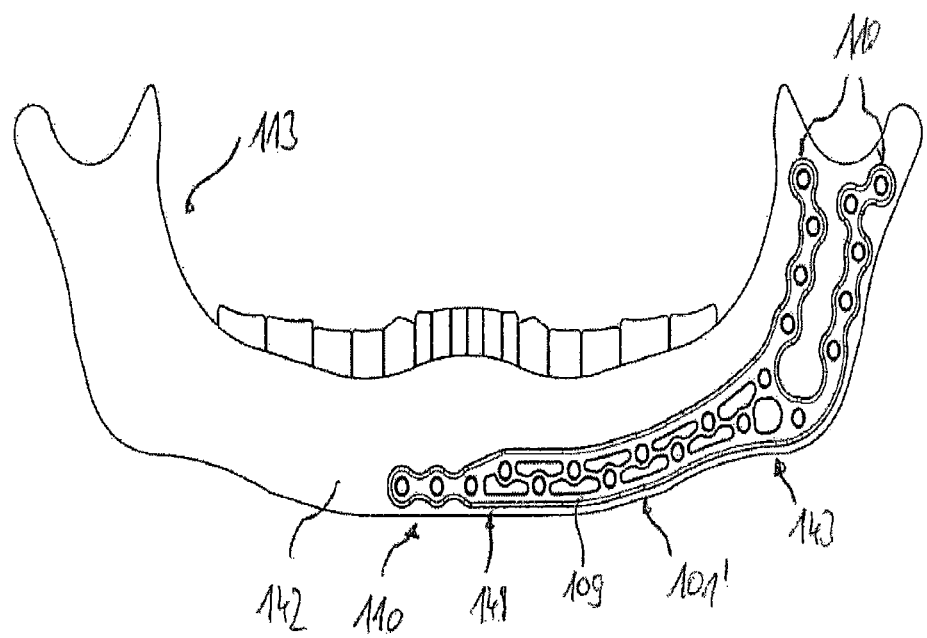
Figure 3A:
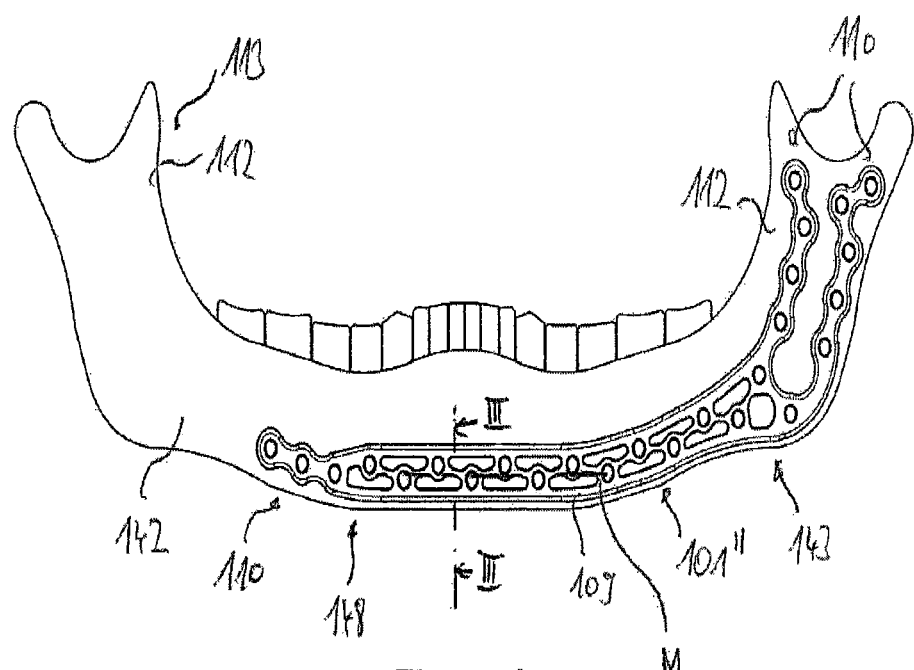
Figure 3B:
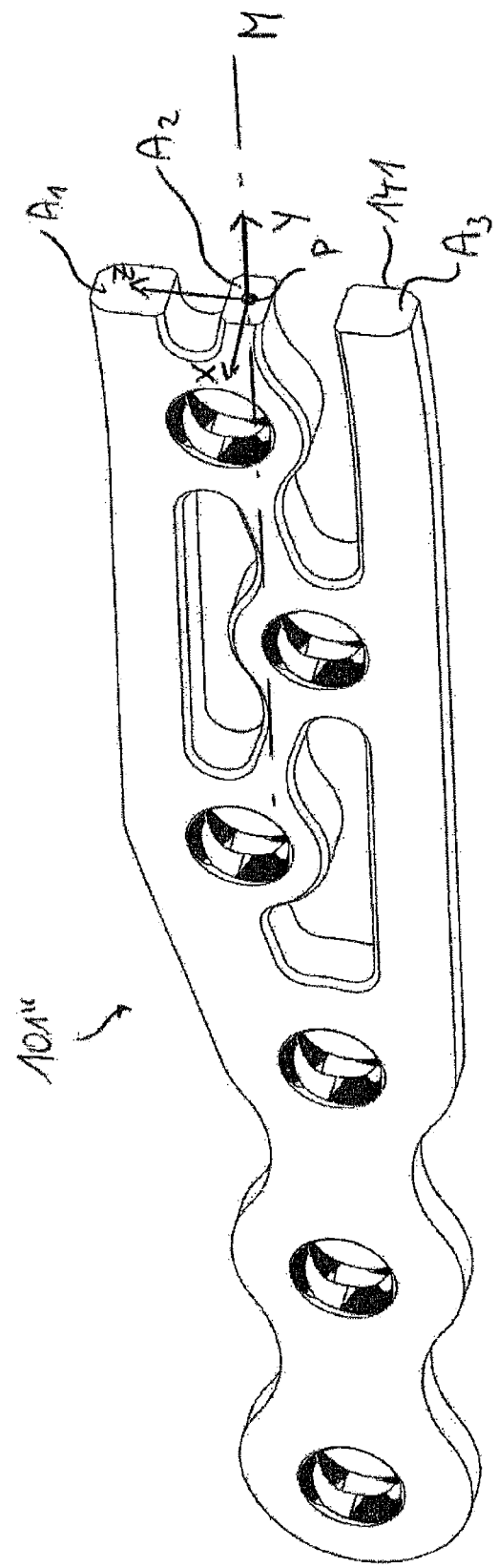
Figure 4B:
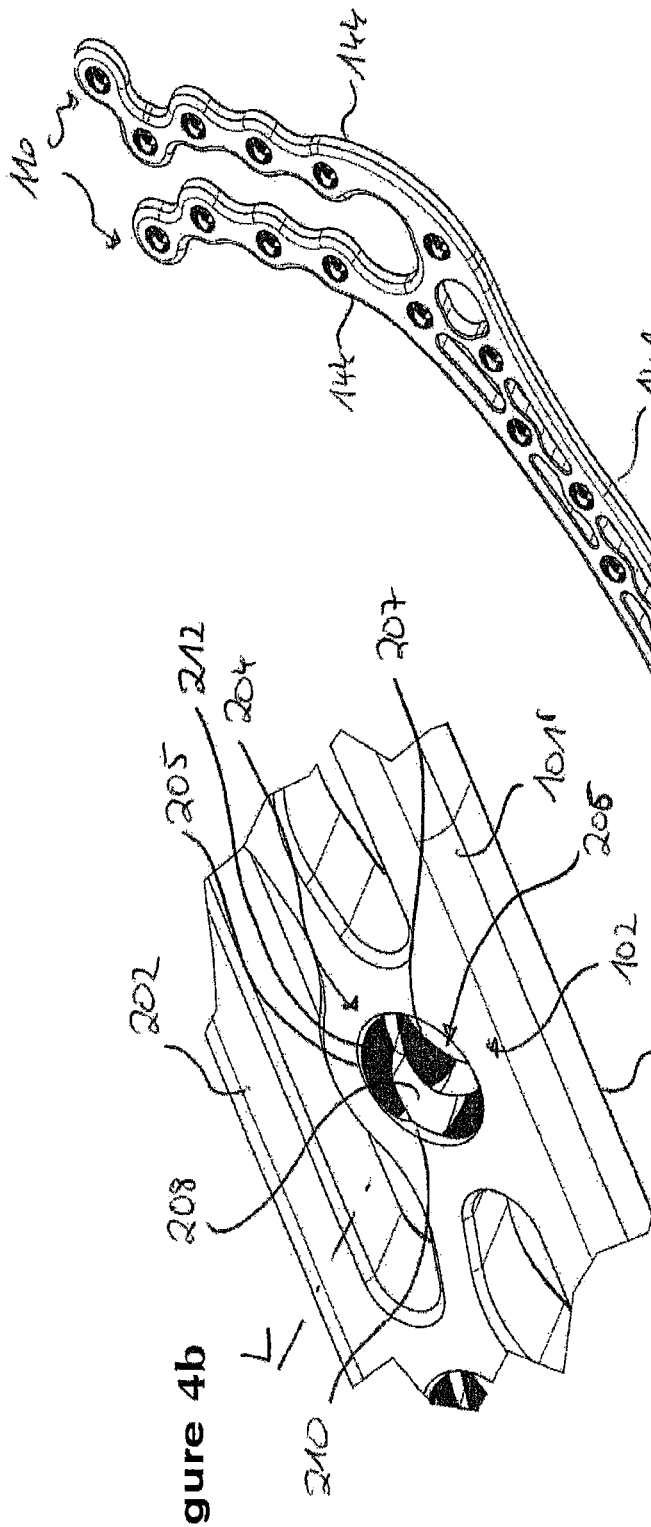
Figure 4A:
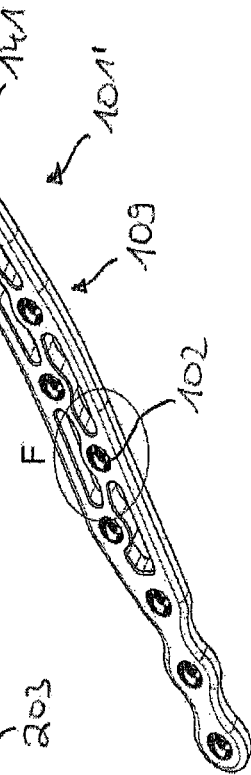
Figure 6B:
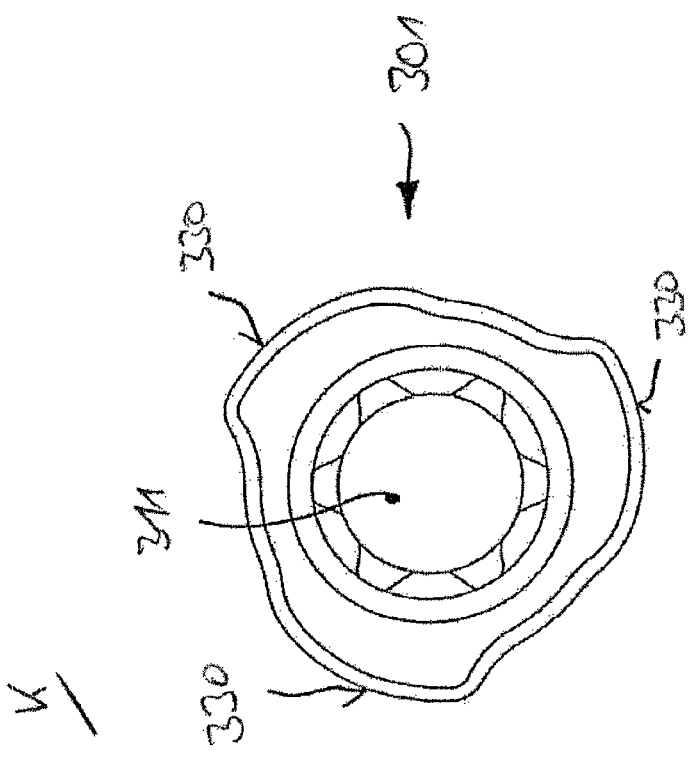
Figure 6A:
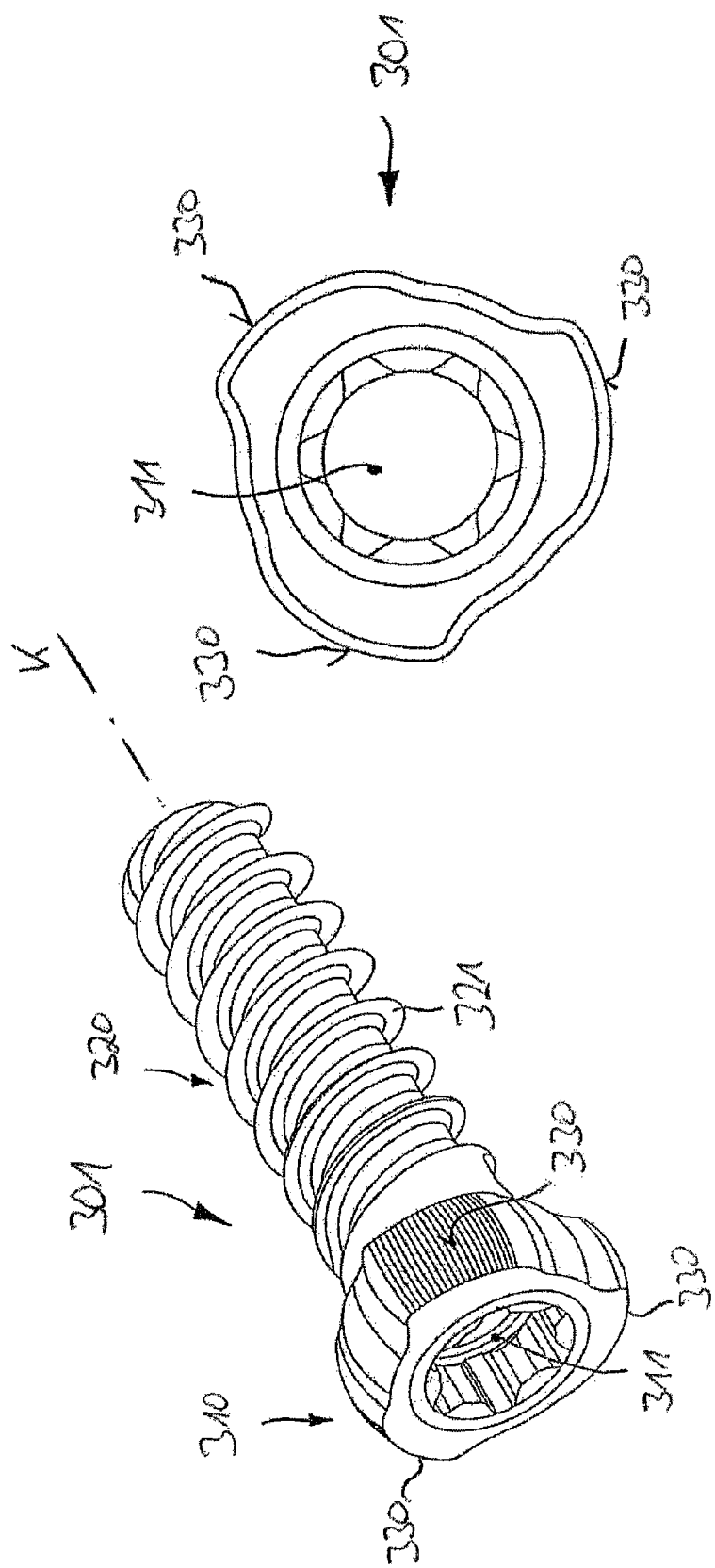
Figure 7:
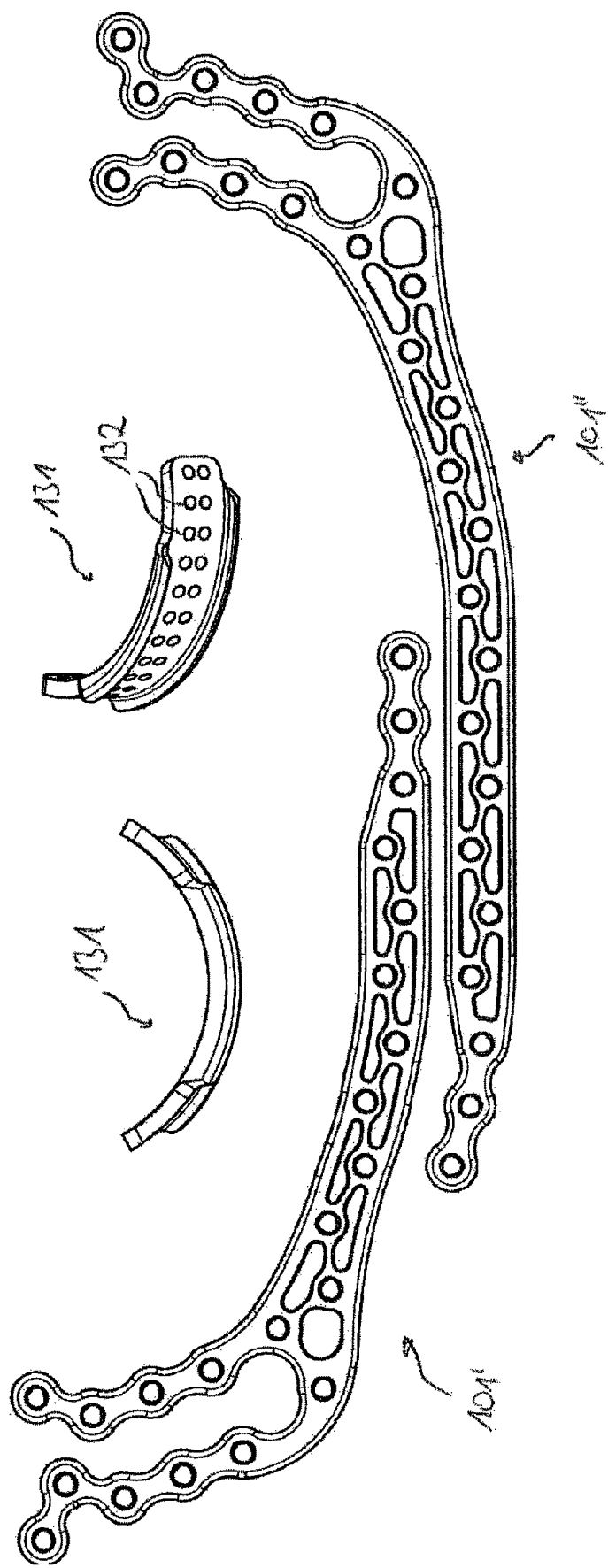
Figure 8:
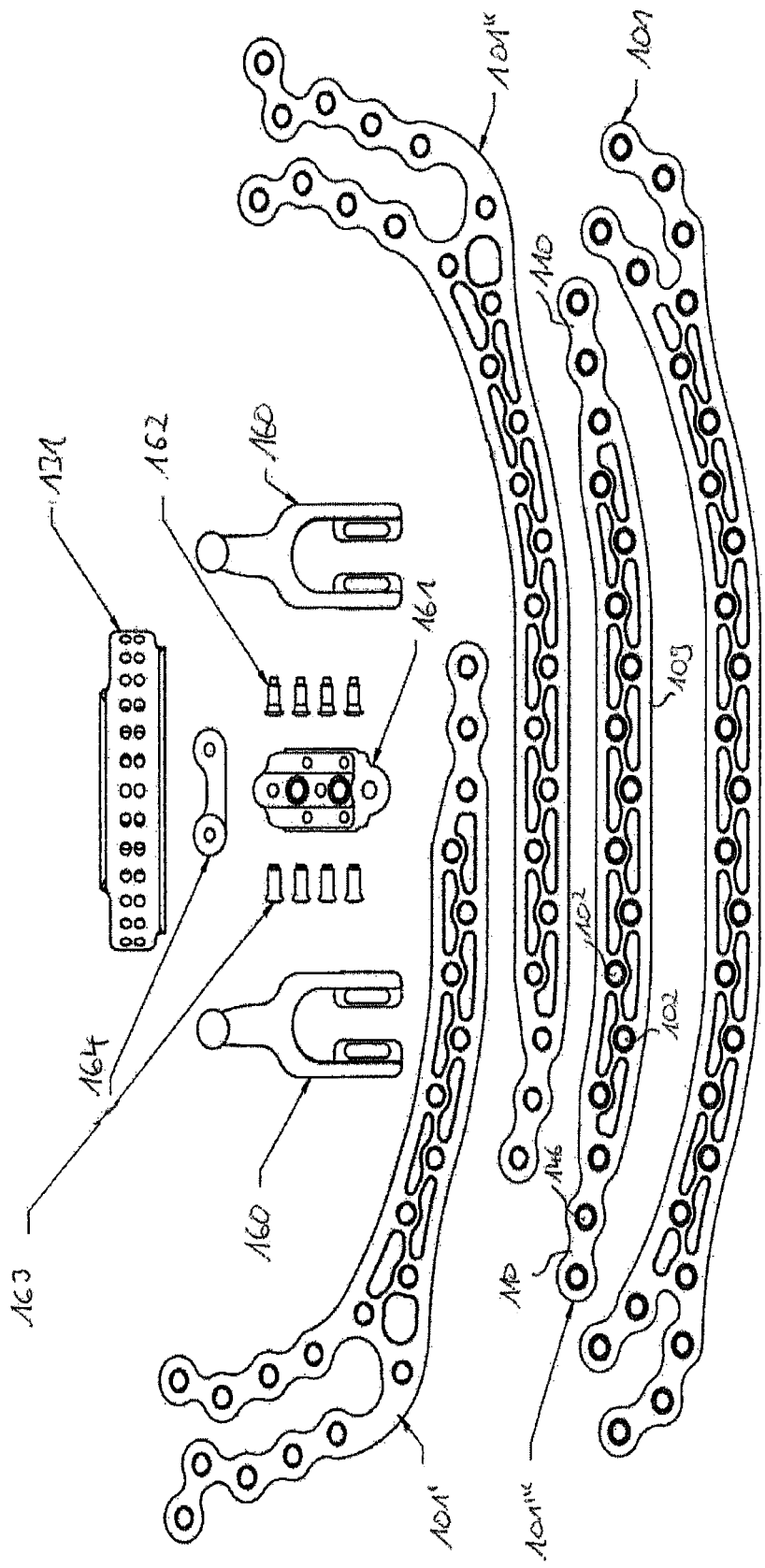
Figure 13A:
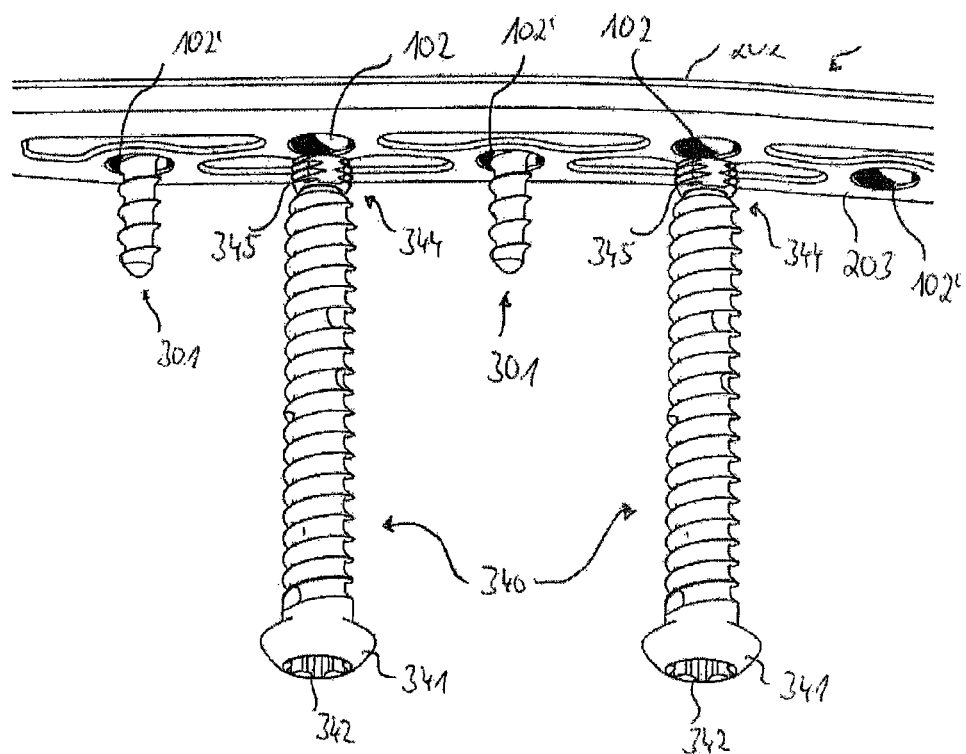
Figure 13B:
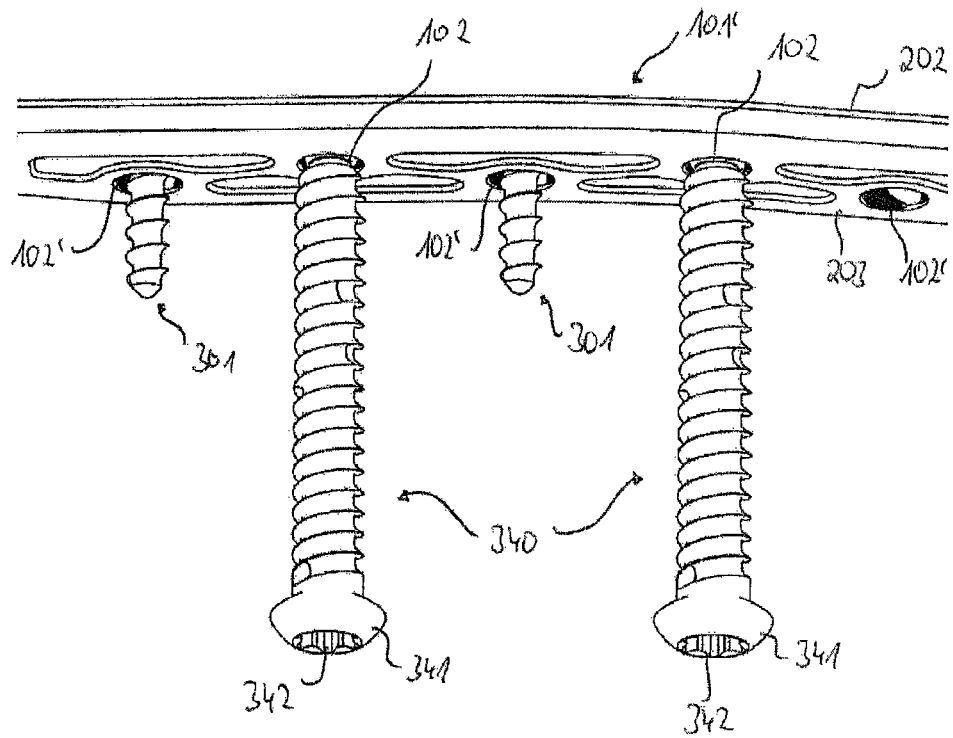
Figure 13C:
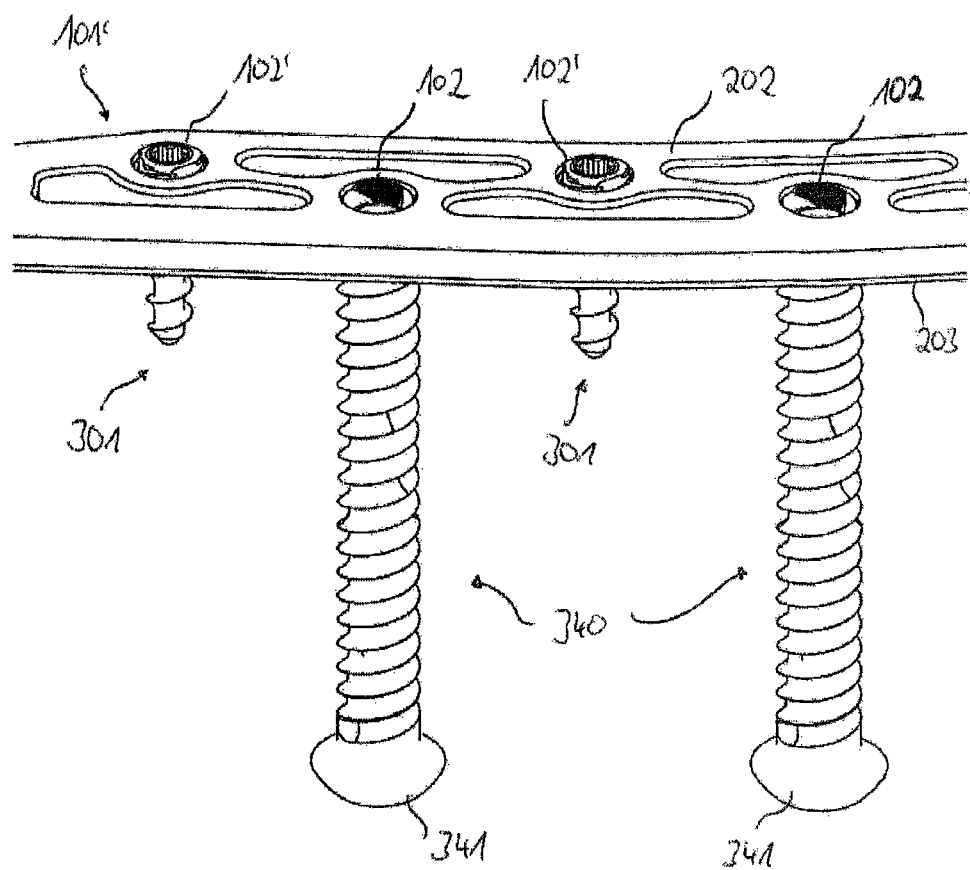

FIGS. 13a to 13c show the bone plate 101' according to the invention from FIG. 2 with two bone screws 340 which are shown in FIGS. 11a and 11b as well as two bone screws 301 which are shown in FIGS. 6a and 6b.

In the view according to FIG. 13a, the shorter bone screws 301 according to FIGS. 6a and 6b are inserted from the top surface 202 of the bone plate 101' in the direction of the bottom surface 203 and pass through the openings 102'. The bone screws 340 according to FIGS. 11a and 11b are directed with their ends 344 toward the bottom surface 203, but are not yet in contact therewith. In the position according to FIG. 13b, the bone screws 340 are inserted and fixed in the openings 102 by means of the blocking elements 345. FIG. 13c includes a perspective view of the top surface 202 of the bone plate 101'.

If sufficient fixing cannot be achieved just with the bone screws 301, the bone screws 340 can provide additional stability. For example, the shorter bone screws 301 can pass through the bone plate 101' and then from the outside into a mandible, and the longer bone screws 340 can pass through the mandible completely from inside to outside and then engage in the bone plate 101'. A conceivable indication is the degradation of a bone which can occur, for example, as a result of previous radiotherapy.

Figure 14A:
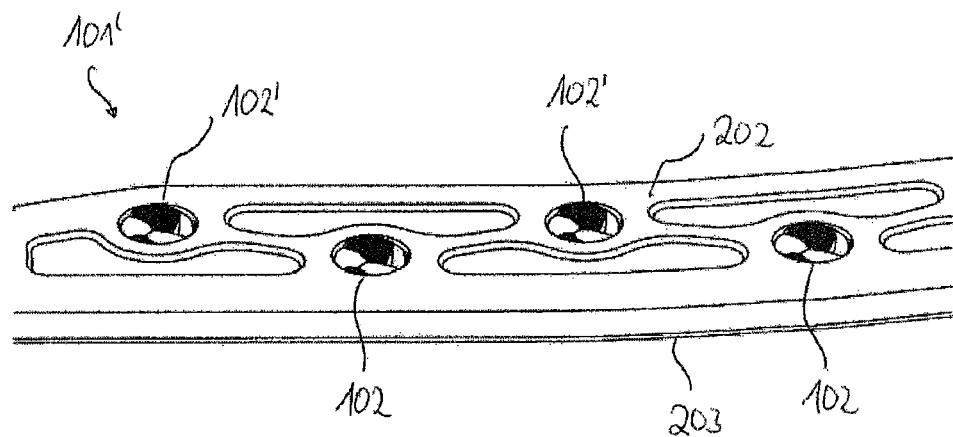
Figure 14B:
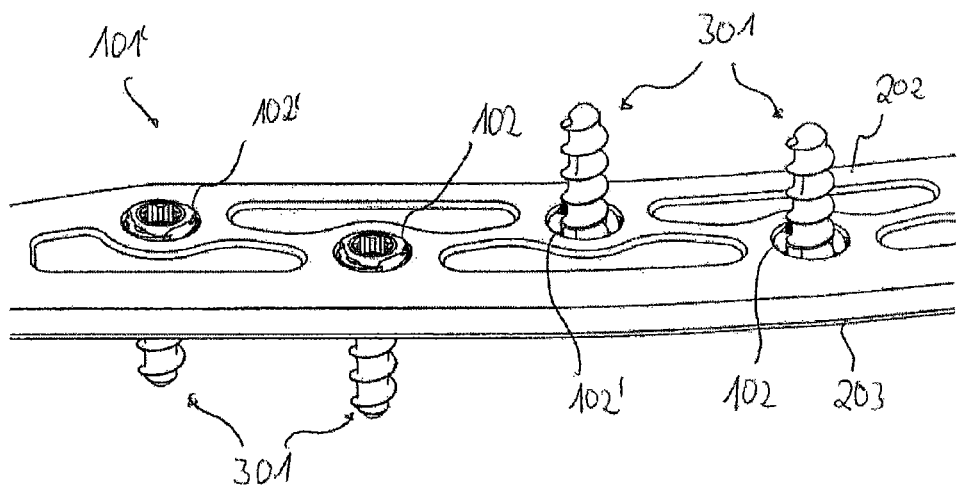

FIGS. 14a and 14b show the same bone plate 101', in the openings 102, 102' of which, however, according to FIG. 14b, four of the shorter bone screws 301 can be inserted. In this case, a first bone screw 301 and a second bone screw 301 pass through the bone plate 101' from the top surface 202 to the bottom surface 203, the first bone screw 301 passing through an opening 102 and the second bone screw 301 passing through an opening 102'. A third bone screw 301 and a fourth bone screw 301 pass through the bone plate 101' from the bottom surface 203 to the top surface 202, the third bone screws 301 passing through an opening 102 and the fourth bone screw 301 passing through an opening 102'.

In a possible application, a first part of the bone plate 101' could be screwed in the region of a mandibular joint from the oral cavity, whilst a second part of the bone plate 101' could be screwed in the corpus region from the outside.

Figure 15A:
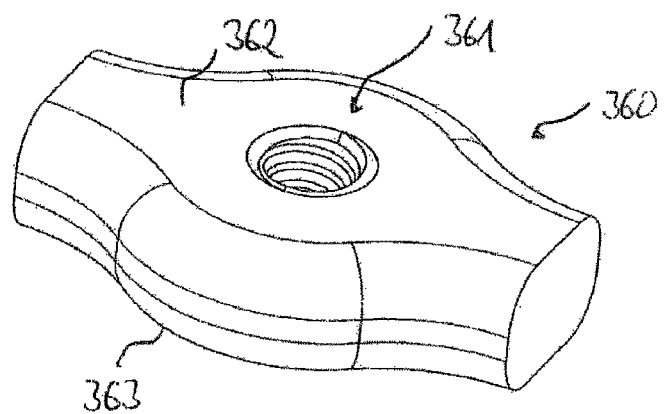
Figure 15B:
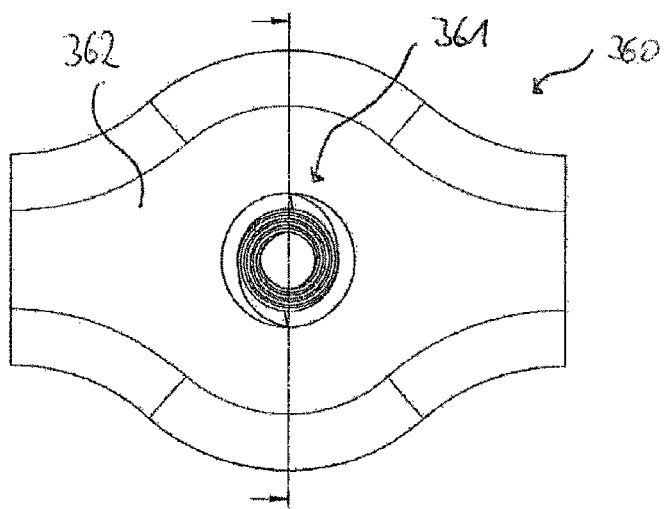
Figure 15C:
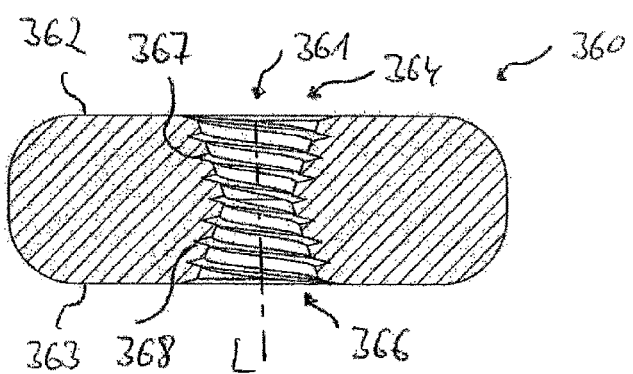

FIGS. 15a to 15c show details of a further bone plate 360, a perspective view of which is shown in FIG. 15a, a top view of which is shown in FIG. 15b and a sectional view of which is shown in FIG. 15c along the cutting line which is marked in FIG. 15b. The bone plate 360 includes an opening 361 which opens out into a first receiving region 364 on a top surface 362 of the bone plate 360 and opens out into a second receiving region 366 on a bottom surface 363. Both the first receiving region 364 and the second receiving region 366 include a cone-shaped internal thread 367 or rather 368 which widens in the direction of the top surface 362 or rather the bottom surface 363. In said exemplary embodiment, both internal threads 367, 368 are identical to one another.

Figure 16A:
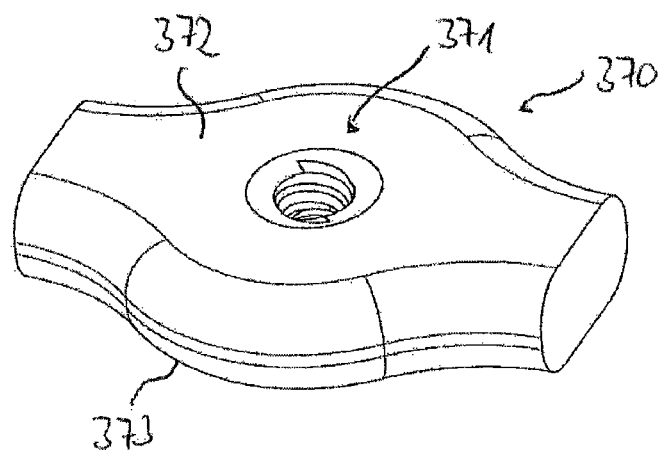
Figure 16B:
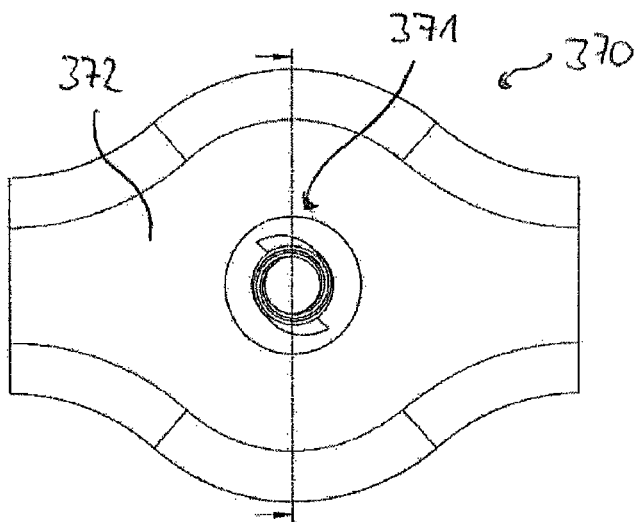
Figure 16C:
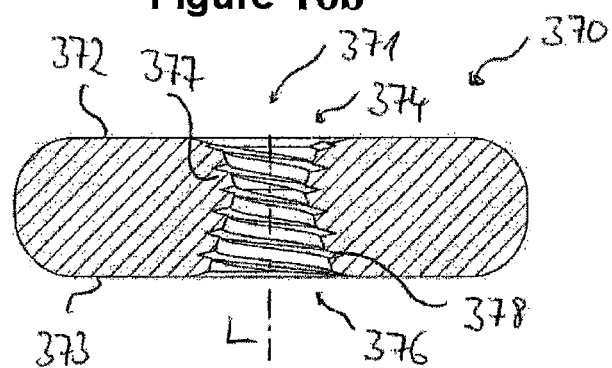

FIGS. 16a to 16c show details of a further bone plate 370, a perspective view of which is shown in FIG. 16a, a top view of which is shown in FIG. 16b and a sectional view of which is shown in FIG. 16c along the cutting line which is marked in FIG. 16b. The bone plate 370 includes an opening 371 which opens out into a first receiving region 374 on a top surface 372 of the bone plate 370 and opens out into a second receiving region 376 on a bottom surface 373. Both the first receiving region 374 and the second receiving region 376 include a cone-shaped internal thread 377 or rather 378 which widens in the direction of the top surface 372 or rather the bottom surface 373. In said exemplary embodiment, only the opening angles of the two internal threads 377, 378 are identical; the first internal thread 377, however, is higher than the second internal thread 378.

Figure 17A:
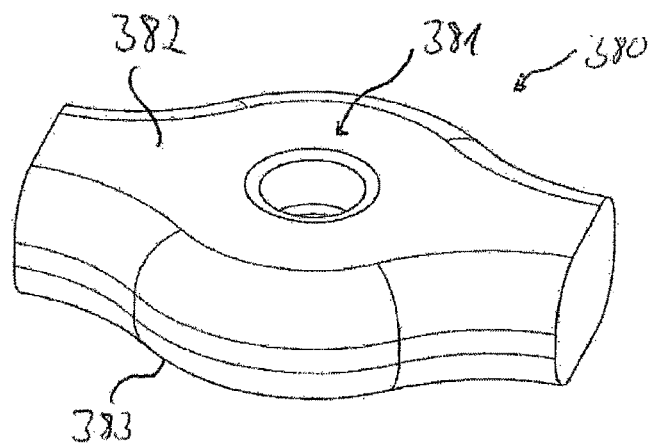
Figure 17B:
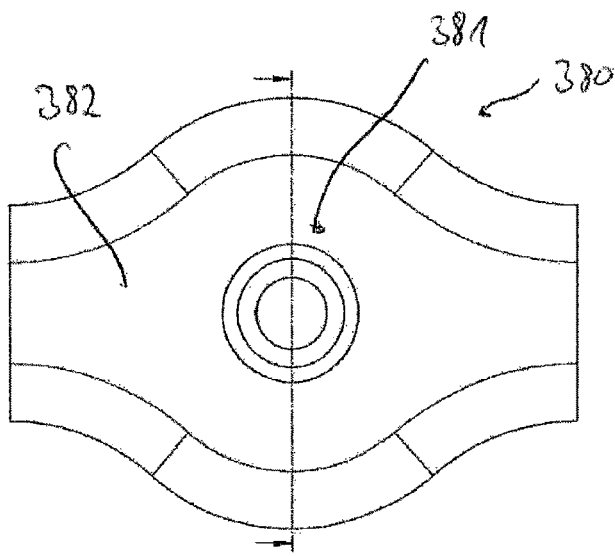
Figure 17C:
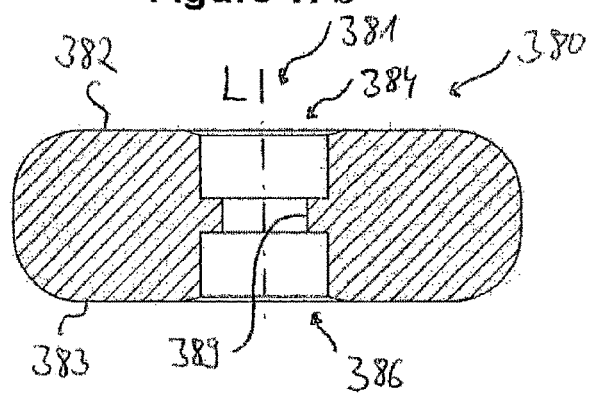

FIGS. 17a to 17c show details of a further bone plate 380, a perspective view of which is shown in FIG. 17a, a top view of which is shown in FIG. 17b and a sectional view of which is shown in FIG. 17c along the cutting line which is marked in FIG. 17b. The bone plate 380 includes an opening 381 which opens out into a first receiving region 384 on a top surface 382 of the bone plate 380 and opens out into a second receiving region 386 on a bottom surface 383. Both the first receiving region 384 and the second receiving region 386 are realized in the shape of a circular cylinder, but do not include any internal threads. An equally circular-cylinder-shaped intermediate region 389 is present between the two receiving regions 384, 386, the radius of which, however, is smaller than that of the receiving regions 384, 386.

Figure 18A:
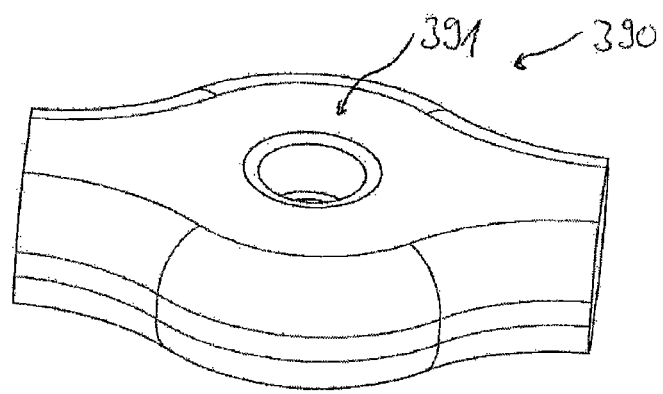
Figure 18B:
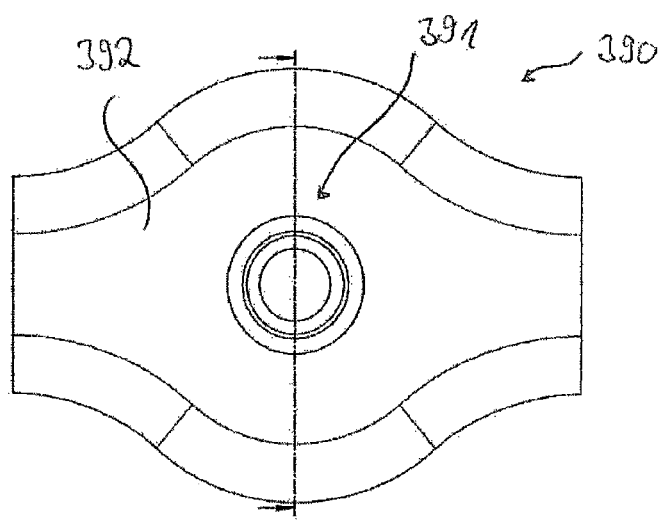
Figure 18C:
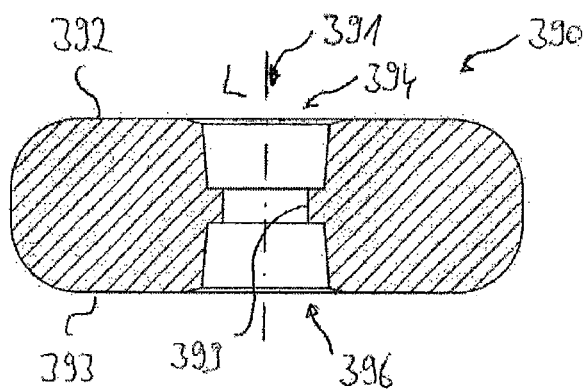

FIGS. 18a to 18c show details of a further bone plate 390, a perspective view of which is shown in FIG. 18a, a top view of which is shown in FIG. 18b and a sectional view of which is shown in FIG. 18c along the cutting line which is marked in FIG. 18b. The bone plate 390 includes an opening 391 which opens out into a first receiving region 394 on a top surface 392 of the bone plate 390 and opens out into a second receiving region 396 on a bottom surface 393. Both the first receiving region 394 and the second receiving region 396 are realized in a cone-shaped manner and widen in the direction of the top surface 392 or rather the bottom surface 393. A circular-cylinder-shaped intermediate region 399 is present between the two receiving regions 394, 396, the radius of which, however, is smaller than the smallest radius of the receiving regions 394, 396.

Bone screws with a slotted screw head (such as, for instance, in CH 669 105 A5) or with a spherical screw head (such as for instance in CH 675 531 A5) can be inserted into the openings 361, 371, 381, 391 of the bone plates 360, 370, 380, 390 which are shown in FIGS. 15a to 18c.

The invention claimed is:

1. A bone plate for reconstruction or trauma treatment of a bone, said bone plate including a main portion having:
  a first end and a second end,
  a first contact surface for contacting and fastening on a first region of the bone, and
  a plurality of receiving means each with at least one opening for receiving, in each case, at least one fastening element,
  wherein at least two wings which are arranged side by side extend at least from the first end of the main portion, which wings each comprise:
    a second contact surface for contacting and fastening on a second region of the bone, and at least one receiving means, each receiving means with at least one opening, each opening for receiving at least one fastening element, wherein the main portion and the at least two wings are realized in such a manner that the main portion has a first minimum bending rigidity with reference to an axis which extends perpendicular to the first contact surface and each of the at least two wings has a respective second minimum bending rigidity with reference to an axis which extends perpendicular to the second contact surface, and the first minimum bending rigidity is greater than each of the second minimum bending rigidities, but smaller than the minimum overall bending rigidity of all of the wings which extend from the first end.

2. The bone plate according to claim 1, wherein the main portion comprises a truss structure.

3. The bone plate as claimed in claim 2, wherein the bone plate is a bone plate for the reconstruction or trauma treatment of a human mandible, the first contact surface is for contacting and fastening on a corpus of the mandible and the second contact surface is for contacting and fastening on an ascending ramus of the mandible.

4. The bone plate as claimed in claim 2, wherein at least one wing does not comprise a truss structure.

5. The bone plate as claimed in claim 2, wherein the main portion is delimited, at least on one side, by at least one frame structure which comprises an outer edge which extends in a substantially rectilinear manner.

6. The bone plate as claimed in claim 2, wherein the main portion has a width within a range of between 2 mm and 20 mm.

7. The bone plate as claimed in claim 2, wherein the main portion has struts which extend transversally with respect to a center line which runs from the first end to the second end of the main portion and the length of the main portion, measured along the center line of the main portion, is within a range of between 25 mm and 300 mm.

8. The bone plate as claimed in claim 2, wherein at least one wing comprises a length which is within a range of between 10 mm and 60 mm.

9. The bone plate as claimed in claim 2, wherein at least one wing comprises a width within a range of between 2 mm and 10 mm.

10. The bone plate as claimed in claim 2, wherein at least one wing comprises a width which is at most 80% of a width of the main portion.

11. The bone plate as claimed in claim 2, wherein said bone plate, perpendicular to the contact surfaces, comprises a thickness which is within a range of between 1 mm and 3 mm.

12. The bone plate as claimed in claim 2, wherein said bone plate is substantially planar and the main portion is deformable, out of a plane defined by the contact surface, into an anatomical form in which it is fastenable on at least part of a mandible substantially only as a result of bending.

13. The bone plate as claimed in claim 2, wherein said bone plate consists of a biocompatible implant material.

14. The bone plate as claimed in claim 1, wherein the opening receives, in each case, at least one bone screw, wherein, in each case, the opening penetrates the bone plate along a longitudinal axis from a top surface to an oppositely situated bottom surface, on the top surface the opening opens out into a first receiving region which is realized for receiving and fixing of a blocking element of a bone screw in a first direction, on the bottom surface, the opening opens out into a second receiving region which is realized for the receiving and fixing of the blocking element in a second direction, and the second direction is substantially opposite the first direction.

15. The bone plate as claimed in claim 14, wherein the first receiving region is delimited by a first inside wall, the second receiving region is delimited by a second inside wall, in each case at least one recess is formed both in the first inside wall and in the second inside wall, and in each of said recesses a distance away from the respective inside wall increases in dependence on the angle of rotation about the longitudinal axis.

16. The bone plate as claimed in claim 15, wherein both the first inside wall and the second inside wall are realized in an at least approximately spherical, paraboloid, ellipsoid or hyperboloid manner in a region of each of the respective recesses.

* * * * *